United States Patent
Tooyama et al.

(10) Patent No.: US 8,956,589 B2
(45) Date of Patent: Feb. 17, 2015

(54) IMAGING DIAGNOSTIC AGENT AND EXTRACORPOREAL DIAGNOSTIC AGENT FOR INCURABLE NEUROLOGICAL DISEASES

(75) Inventors: Ikuo Tooyama, Otsu (JP); Hiroyasu Taguchi, Otsu (JP); Shigehiro Morikawa, Otsu (JP); Makoto Urushitani, Otsu (JP); Daijiro Yanagisawa, Otsu (JP); Tomone Nagae, Tottori (JP); Nobuaki Shirai, Ritto (JP); Koichi Hirao, Ritto (JP); Masanari Kato, Kusatsu (JP); Hirohiko Kimura, Kusatsu (JP); Takashi Okada, Kusatsu (JP)

(73) Assignee: Shiga University of Medical Science, Shiga (JP)

( * ) Notice: Subject to any disclaimer, the term of this patent is extended or adjusted under 35 U.S.C. 154(b) by 328 days.

(21) Appl. No.: 13/203,589

(22) PCT Filed: Feb. 26, 2010

(86) PCT No.: PCT/JP2010/053590
§ 371 (c)(1),
(2), (4) Date: Aug. 26, 2011

(87) PCT Pub. No.: WO2010/098502
PCT Pub. Date: Sep. 2, 2010

(65) Prior Publication Data
US 2011/0311444 A1    Dec. 22, 2011

(30) Foreign Application Priority Data

Feb. 27, 2009  (JP) ................................. 2009-045531
Feb. 27, 2009  (JP) ................................. 2009-045705

(51) Int. Cl.
*A61K 49/06*   (2006.01)
*C07C 69/738*  (2006.01)
(Continued)

(52) U.S. Cl.
CPC ............ *G01N 33/6896* (2013.01); *A61K 49/10* (2013.01); *A61K 51/04* (2013.01); *C07C 49/255* (2013.01); *C07C 59/70* (2013.01); *C07C 59/90* (2013.01); *C07C 69/738* (2013.01); *C07C 225/22* (2013.01); *C07C 235/78* (2013.01); *C07C 255/40* (2013.01);
(Continued)

(58) Field of Classification Search
USPC ......... 514/532, 533, 539, 545, 619, 621, 679; 424/1.81, 1.89, 9.1, 1.65, 529, 0.81; 564/168, 169, 264, 443
See application file for complete search history.

(56) References Cited

U.S. PATENT DOCUMENTS

2007/0060644 A1    3/2007   Vander Jagt et al.
2008/0161391 A1*   7/2008   Lee et al. ...................... 514/473
(Continued)

FOREIGN PATENT DOCUMENTS

| WO | 03/106439    | 12/2003 |
| WO | 2005/042461  | 5/2005  |
| WO | 2007/044867  | 4/2007  |
| WO | 2007/111179  | 10/2007 |
| WO | 2008/045534  | 4/2008  |

OTHER PUBLICATIONS

International Search Report issued Apr. 27, 2010 in International (PCT) Application No. PCT/JP2010/053590, of which the present application is the national stage.
(Continued)

*Primary Examiner* — Michael G Hartley
*Assistant Examiner* — Jagadishwar Samala
(74) *Attorney, Agent, or Firm* — Wenderoth, Lind & Ponack, L.L.P.

(57) ABSTRACT

Disclosed are a curcumin derivative or a salt thereof, which contains a fluorine atom, represented by formula (I):

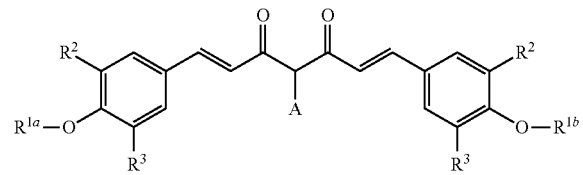

(wherein $R^{1a}$ and $R^{1b}$ are each independently a hydrogen atom, alkyl, acetyl, or methoxycarbonyl; $R^2$s are each independently a fluorine atom, $CHF_2$—, $CF_3$—, $CHF_2O$—, or $CF_3O$—; $R^3$s are each independently a hydrogen atom or a fluorine atom; A is alkyl, cyano, carboxyl, alkoxycarbonyl, or $R^4$—$(CH_2)_m$—; $R^4$ is hydroxy, carboxy, cyano, acetyloxy, alkoxycarbonyl, alkoxyalkoxy, hydroxyalkoxy, or $CONR^5R^6$; $R^5$ and $R^6$ are each independently a hydrogen atom or alkyl; and m is an integer from 1 to 5), and a diagnostic imaging agent for diagnosing a disease in which an amyloid β peptide aggregate accumulates, the diagnostic imaging agent containing a compound having a 1,3-dicarbonyl structure, wherein the compound exists in a keto form and an enol form, and the keto form and the enol form have different affinities, respectively, to the amyloid β peptide aggregate.

7 Claims, 11 Drawing Sheets

(51) Int. Cl.
 *A61K 31/12* (2006.01)
 *G01N 33/68* (2006.01)
 *A61K 49/10* (2006.01)
 *A61K 51/04* (2006.01)
 *C07C 49/255* (2006.01)
 *C07C 59/70* (2006.01)
 *C07C 59/90* (2006.01)
 *C07C 225/22* (2006.01)
 *C07C 235/78* (2006.01)
 *C07C 255/40* (2006.01)
 *C07D 213/50* (2006.01)
 *C07D 307/46* (2006.01)

(52) U.S. Cl.
 CPC ............ *C07D 213/50* (2013.01); *C07D 307/46* (2013.01); *G01N 33/6839* (2013.01); *G01N 2800/2821* (2013.01)
 USPC .......... 424/1.65; 514/332; 514/532; 514/533; 514/545; 514/541

(56) References Cited

U.S. PATENT DOCUMENTS

| | | | |
|---|---|---|---|
| 2009/0004107 | A1 | 1/2009 | Mukherjee et al. |
| 2009/0263492 | A1* | 10/2009 | Cashman et al. ............ 424/529 |
| 2009/0264732 | A1 | 10/2009 | Ross et al. |
| 2010/0240905 | A1 | 9/2010 | Raja et al. |
| 2011/0208064 | A1* | 8/2011 | Chongzhao et al. ......... 600/476 |
| 2012/0095051 | A1* | 4/2012 | Johnson et al. ............... 514/332 |

OTHER PUBLICATIONS

H. Lee et al., Chemometric Studies on Brain-uptake of PET Agents via VolSurf Analysis, Bull. Korean Chem. Soc., vol. 29, No. 1, 2008, pp. 61-68.

E. Ryu et al., Curcumin and Dehydrozingerone Derivatives: Synthesis, Radiolabeling, and Evaluation for β-Amyloid Plaque Imaging, J. Med. Chem., 49, 2006, pp. 6111-6119.

D. Schenk et al., Immunization with amyloid-β attenuates Alzheimer-disease-like pathology in the PDAPP mouse, Nature, vol. 400, pp. 173-177, 1999.

J. Hardy et al., The Amyloid Hypothesis of Alzheimer's Disease: Progress and Problems on the Road to Therapeutics, Science, vol. 297, pp. 353-356, 2002.

N. Okamura et al., Progress in imaging amyloid, Dementia Japan, vol. 20, pp. 216-225, 2006.

Yang et al., Curcumin Inhibits Formation of Amyloid β Oligomers and Fibrils, Binds Plaques, and Reduces Amyloid in Vivo, Journal of Biological Chemistry, vol. 280, No. 7: pp. 5892-5901, 2005.

M. Higuchi et al., $^{19}$F and $^1$H MRI detection of amyloid β plaques in vivo, Nature Neuroscience, vol. 8, No. 4, pp. 527-533, Apr. 2005.

O. Hansson et al., Association between CSF biomarkers and incipient Alzheimer's disease in patients with mild cognitive impairment: a follow up study, Lancet Neurology, vol. 5, pp. 228-234, Mar. 2006.

E. Matsubara, Aβ oligomer, Dementia Japan, vol. 21, pp. 253-260, 2007.

M. Lambert et al., Monoclonal antibodies that target pathologies assemblies of Aβ, Journal of Neurochemistry, vol. 100, pp. 23-35, 2007.

* cited by examiner

A. COLORS AND CHROMATIC SPECTRA OF DMSO SOLUTIONS HAVING DIFFERENT CONCENTRATIONS IN WHICH COMPOUND 1 IS DISSOLVED AT 20 μg/ml

B. ENOL RATE (HORIZONTAL AXIS) CALCULATED FROM NMR PEAK AND 550 nm ABSORBANCE

A: COMPOUND ONLY
B: COMPOUND AND Aβ PEPTIDE BEFORE AGGLUTINATION
C: COMPOUND AND Aβ AGGREGATE
D: Aβ AGGREGATE ONLY

IMAGING DIAGNOSTIC AGENT AND EXTRACORPOREAL DIAGNOSTIC AGENT FOR INCURABLE NEUROLOGICAL DISEASES

TECHNICAL FIELD

The present invention relates to a new curcumin derivative or a salt thereof that is useful for diagnostic imaging of a disease in which amyloid β proteins accumulate, a diagnostic imaging agent whose active component is the new curcumin derivative or the salt thereof, and a staining agent for amyloid β proteins or senile plaques. Further, the present invention relates to a diagnostic imaging agent and an in-vitro diagnostic agent, for a disease in which amyloid β peptide aggregates accumulate, which utilize a keto-enol tautomerism.

BACKGROUND ART

Alzheimer's disease is a disease characterized by progressive dementia occurring from presenium to old age, and the number of domestic patients suffering the disease is said to be one million or more at present. It is anticipated that the number will certainly increase in the future in association with the aging population. Clinical symptoms of Alzheimer's disease are memory disorder, higher brain dysfunction (aphasia, apraxia, agnosia, and constructional apraxia), and the like. The symptoms are often observed commonly in other dementing disorders, and it is very difficult to make a definitive diagnosis of Alzheimer's disease only by the clinical symptoms. There has been no basic remedy for Alzheimer's disease to date. However, since a vaccine therapy was successful in model mice in 1999, there have been increasing expectations for development of basic remedies (non-patent literature 1). In order to effectively use such basic remedies, it is necessary to diagnose Alzheimer's disease in an early stage.

On the other hand, histopathological characteristics to determine Alzheimer's disease include senile plaques and neurofibrillary tangles. Main components of the former are amyloid β proteins which have β-sheet structures, and main components of the latter are hyperphosphorylated tau proteins. At present, an amyloid hypothesis is dominant in which a serious pathological change initially occurring at the onset of Alzheimer's disease is accumulation of amyloid β peptides (non-patent literature 2). It is known that in Alzheimer's disease, well before the onset of clinical symptoms, the above pathologic tissue change such as accumulation of amyloid β proteins has started in the brain. Therefore, detection of intracerebral amyloid β proteins as a marker will serve as one method for early diagnosis of the diseases in which amyloids accumulate, especially, Alzheimer's disease.

In such a view point, in recent years, radioactive contrast media have been studied that selectively bind to intracerebral amyloid β proteins for use in positron emission tomography (PET) and single-photon emission computed tomography (SPECT) (non-patent literature 3). As classical compounds having a high affinity to amyloids include congo red, thioflavin S, and thioflavin T, which are used in pathologic definitive diagnosis of Alzheimer's disease. It is difficult for many of them to pass through the blood-brain barrier, and even if they are intravenously administered, they hardly move into the brain. Moreover, recently, various structures have been found to have amyloid affinities, and one of those is curcumin (non-patent literature 4). Therefore, contrast media have been studied in consideration of the transmissiveness through the blood-brain barrier, and contrast media such as ISB, PIB, BF-168, (patent literature 1) and the like have been developed. Some of them have good results in clinical trials. However, since such contrast media use radionuclides such as $^{11}C$, $^{13}N$, $^{15}O$, $^{18}F$, and the like, there is a concern about adverse reaction due to radiation injuries, and in addition, a cyclotron facility needs to be provided nearby. Therefore, a diagnostic method that does not use radionuclides is desired.

As an example of a diagnostic method that does not use radionuclides is nuclear magnetic resonance imaging method (MRI). Recently, there have been reports that imaging of senile plaques by use of $^{19}F$-MRI was successful (patent literature 2, patent literature 3, and non-patent literature 5), and realization of such MRI diagnosis is highly expected. However, it is known that MRI is low in detectivity compared with PET and the like. Therefore, it is highly desired that high sensitivity MRI contrast media are developed for establishing a safe diagnosis method for Alzheimer's disease.

Further, with respect to in-vitro diagnostic agents, ELISA using specific antibodies for amyloid β peptides is being studied (non-patent literature 6). Recently, a hypothesis has become more dominant that a causative substance for neuronal cell deaths in Alzheimer's disease is rather not amyloid β peptides themselves but aggregates of amyloid β peptides such as amyloid β peptide oligomers (non-patent literature 7). Conventional ELISA which uses specific antibodies for amyloid β peptides can determine the quantity of amyloid β peptides in cerebrospinal fluid and serum, but cannot specifically detect aggregates of amyloid β peptides such as amyloid β peptide oligomers, the aggregates being considered as causing neurotoxicity.

Therefore, based on the hypothesis that the aggregates of amyloid β peptides such as amyloid β peptide oligomers are the cause for neuronal cell deaths occurring in Alzheimer's disease, methods and materials for specifically detecting aggregates of amyloid β peptides such as amyloid β peptide oligomers are being developed. Production of an antibody that specifically reacts with amyloid β peptide oligomers has been reported to date (non-patent literature 8). In a case where an antibody is used as an in-vitro diagnostic agent, it is necessary to perform cumbersome operations such as ELISA, which require several hours or more for conducting measurements. Moreover, an antibody is a high molecular weight protein, hardly passes through the blood-brain barrier, and thus cannot be used as a diagnostic imaging agent.

With respect to a contrast medium for MR imaging, a material having a nature of binding to amyloid β peptides is labeled with fluorine ($^{19}F$), and is caused to bind to senile plaques appearing in the brain of an Alzheimer's disease patient. Then, a signal of $^{19}F$ is detected, thereby imaging the senile plaques (non-patent literature 5, mentioned above). Generally, in any compound, a $^{19}F$ signal is strong when the material is in a free state, and the $^{19}F$ signal becomes weak when the material binds to a senile plaque. Therefore, a material is more desired that has a nature that the material locally repeats binding to and getting released from a senile plaque at a part where senile plaques are present, than a material that merely binds to a senile plaque.

With respect to a contrast medium for PET, a material having a nature of binding to amyloid β peptides is radioactively labeled and is caused to bind to a senile plaque appearing in the brain of an Alzheimer's disease patient, thereby imaging the senile plaque (non-patent literature 3, mentioned above). A radioactively-labeled material would cause fewer adverse reactions such as radiation injuries if it is removed in a short period of time. Therefore, it is desired that, after the material binds to a senile plaque and imaging is finished, the material is released from the senile plaque to be promptly excreted.

A keto-enol tautomerism is a nature of a compound indicating a difference between structures that the compound takes. Such a compound is present in an equilibrium mixture of a keto form and an enol form thereof. Therefore, depending on the environment, the compound exists, with a rate of the keto form higher than that of the enol form, or a rate of the enol form higher than that of the keto form. Moreover, the keto form and the enol form have various differences with each other, such as different colors, different absorption spectra, different fluorescence emissions, and different interactions with other substances, due to their structures. However, no reagent or diagnostic agent that focuses on and actively uses this phenomenon, the keto-enol tautomerism, has been developed.

It is known that curcumin having a 1,3-dicarbonyl structure binds to amyloid β peptides as described above (non-patent literature 4, mentioned above), and application thereof to a diagnostic imaging agent for Alzheimer's disease is being examined, which does not, however, positively utilizes the keto-enol tautomerism.

CITATION LIST

Patent Literature

[PTL 1]: WO 03/106439
[PTL 2]: WO 2005/042461
[PTL 3]: WO 2007/111179

Non-patent Literature

[NPL 1]: Schenk D, Barbour R, Dunn W, Gordon G, Grajeda H, Guido T, Hu K, Huang J, Johnson-Wood K, Khan K, Kholodenko D, Lee M, Liao Z, Lieberburg I, Motter R, Mutter L, Soriano F, Shopp G, Vasquez N, Vandevert C, Walker S, Wogulis M, Yednock T, Games D, Seubert P: Immunization with amyloid-beta attenuates Alzheimer-disease-like pathology in the PDAPP mouse. Nature 400:173-177, 1999.
[NPL 2]: Hardy J, Selkoe D J: The amyloid hypothesis of Alzheimer's disease: progress and problems on the road to therapeutics. Science 297:353-356, 2002.
[NPL 3]: Nobuyuki Okamura, Kazuhiko Yanai, Yukitsuka Kudo: Progress in imaging amyloid, Dementia Japan 20: 216-225, 2006.
[NPL 4]: Yang F, Lim G P, Begum A N, Ubeda O J, Simmons M R, Ambegaokar S S, Chen P, Kayed R, Glabe C G, Frautschy S A, Cole G M: Curcumin inhibits formation of amyloid β oligomer and fibrils, binds plaques, and reduces amyloid in vivo. Journal of Biological Chemistry 280(7): 5892-5901, 2005.
[NPL 5]: Higuchi M, Iwata N, Matsuba Y, Sato K, Sasamoto K, Saido C T: $^{19}F$ and $^1H$ MRI detection of amyloid beta plaques in vivo. Nat. Neurosci. 8:527-533, 2005.
[NPL 6]: Hansson O, Zetterberg H, Buchhave P, Londos E, Blennow K, Minthon L: Association between CSF biomarkers and incipient Alzheimer's disease in patients with mild cognitive impairment: a follow-up study. Lancet Neurol 5: 228-234, 2006.
[NPL 7]: Etsuro Matsubara: Aβ oligomer, Dementia Japan 21: 253-260, 2007.
[NPL 8]: Lambert M P, Velasco P T, Chang L, Viola K L, Fernandez S, Lacor P N, Khuon D, Gong Y, Bigio E H, Shaw P, De Felice F G, Krafft G A, Klein W L: Monoclonal antibodies that target pathological assemblies of Abeta. J Neurochem 100: 23-35, 2007.

SUMMARY OF INVENTION

Technical Problem

An object of the present invention is to provide a substance having a high binding specificity to and a high detectivity of an amyloid β protein, the substance being appropriate for an MRI contrast medium for diagnosis of Alzheimer's disease.

Further, an object of the present invention is to provide a diagnostic imaging agent, an in-vitro diagnostic agent, and a diagnostic method, which utilize a keto-enol tautomerism which a certain kind of compound has, and a nature that the enol form and the keto form of the compound have different affinities, respectively, to the amyloid β peptide aggregate. The diagnostic imaging agent, the in-vitro diagnostic agent, and the diagnostic method are directed to a disease in which an amyloid β peptide aggregate, which is a causative substance of Alzheimer's disease, accumulates.

Solution to Problem

In order to solve the above problems, the present inventors diligently studied and found that a compound having a certain chemical structure containing F atoms has a high binding specificity to an amyloid β protein, and have completed the present invention.

The keto-enol tautomerism is a known nature of a certain kind of compound, which has been known for a long time. However, this nature has not been tried to be applied to a diagnostic agent for a disease. If this nature is utilized in a diagnostic agent, means for developing a new drug can be provided. The present inventors found that a certain kind of compound has the keto-enol tautomerism and a nature that the enol form and the keto form have different affinities, respectively, to the amyloid β peptide aggregate, which is a causative substance of Alzheimer's disease. That is, the compound has a nature that the compound repeatedly binds to or is released from an amyloid β peptide aggregate at a certain rate, under various environments in and out of a living body.

The present invention has been completed base on these findings, and provides the following compound, diagnostic imaging agent, in-vitro diagnostic agent, diagnostic method, and the like.

Item 1. A curcumin derivative or a salt thereof represented by formula (I):

[Chem. 1]

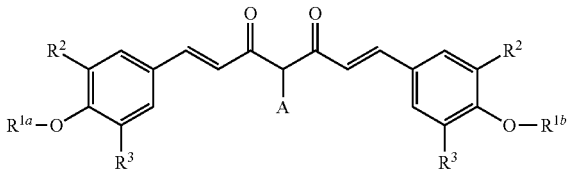

(wherein $R^{1a}$ and $R^{1b}$ are each independently a hydrogen atom, alkyl, acetyl, or methoxycarbonyl; $R^2$s are each independently a fluorine atom, $CHF_2-$, $CF_3-$, $CHF_2O-$, or $CF_3O-$; $R^3$s are each independently a hydrogen atom or a fluorine atom; A is alkyl, cyano, carboxyl, alkoxycarbonyl, or $R^4-(CH_2)_m-$; $R^4$ is hydroxy, carboxy, cyano, acetyloxy, alkoxycarbonyl, alkoxyalkoxy, hydroxyalkoxy, or CONR$^5$R$^6$; R$^5$ and R$^6$ are each independently a hydrogen atom or alkyl; and m is an integer from 1 to 5).

Item 2. The curcumin derivative or the salt thereof according to item 1, wherein m is 1 to 3.

Item 3. A diagnostic imaging agent, for a disease in which an amyloid β protein accumulates, whose active component is the curcumin derivative or the salt thereof according to item 1 or 2.

Item 4. The diagnostic imaging agent according to item 3, wherein the disease in which the amyloid β protein accumulates is Alzheimer's disease.

Item 5. The diagnostic imaging agent according to item 3 or 4, wherein diagnostic imaging is MRI.

Item 6. A diagnostic method, using the diagnostic imaging agent according to item 3, for a disease in which a β-sheet structure of a protein is a cause of the disease or a part of the cause of the disease.

Item 7. A staining agent, for an amyloid β protein in tissue or a senile plaque in the brain, whose active component is the curcumin derivative or the salt thereof according to item 1 or 2.

Item 8. A method for staining an amyloid β protein in tissue or a senile plaque by using the staining agent according to item 7.

Item 9. A diagnostic imaging agent for diagnosing a disease in which an amyloid β peptide aggregate accumulates, the diagnostic imaging agent comprising a compound having a 1,3-dicarbonyl structure, wherein the compound exists in a keto form and an enol form, and the keto form and the enol form have different affinities, respectively, to the amyloid β peptide aggregate.

Item 10. The diagnostic imaging agent according to item 9, wherein the compound is a compound in which the enol form has a higher affinity to the amyloid β peptide aggregate than the keto form.

Item 11. The diagnostic imaging agent according item 9 or 10, wherein the compound is a compound having a substituent at the second position of the 1,3-dicarbonyl structure.

Item 12. The diagnostic imaging agent according to any one of items 9 to 11, wherein the compound is a compound represented by formula (i):

[Chem. 2]

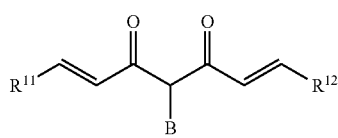

(wherein R$^{11}$ and R$^{12}$ are each independently an aryl group or a heteroaryl group that may be substituted, and B is hydrogen or an alkyl group that may be substituted.)

Item 13. The diagnostic imaging agent according to any one of items 9 to 12, wherein the disease in which the amyloid β peptide aggregate accumulates is Alzheimer's disease.

Item 14. The diagnostic imaging agent according to any one of items 9 to 13, being a nuclear magnetic resonance (MR) diagnostic imaging agent.

Item 15. The diagnostic imaging agent according to any one of items 9 to 13, wherein the compound contains a positron emitting nuclide, and the diagnostic imaging agent is a positron emission tomography (PET) diagnostic imaging agent.

Item 16. A diagnostic method, using the diagnostic imaging agent according to any one of items 9 to 13, for a disease in which an amyloid β peptide aggregate accumulates.

Item 17. An in-vitro diagnostic agent for diagnosing a disease in which an amyloid β peptide aggregate accumulates, the in-vitro diagnostic agent comprising a compound having a 1,3-dicarbonyl structure, wherein the compound exists in a keto form and an enol form, the enol form has a higher affinity to the amyloid β peptide aggregate than the keto form.

Item 18. A diagnostic method, using the in-vitro diagnostic agent according to item 17, for a disease in which an amyloid β peptide aggregate accumulates.

Advantageous Effects of Invention

The compound of the present invention has a high affinity to an amyloid β protein and a high blood-brain barrier transmissiveness, and is useful as an active component for a diagnostic imaging agent for a disease in which the amyloid β protein accumulates. In particular, since the compound of the present invention contains F atoms, it is useful as an active component of a $^{19}$F-MRI contrast medium. Further, the compound of the present invention is useful as an active component of a staining agent, for example, as a fluorescent staining agent, for an amyloid β protein in tissue such as brain or a senile plaque. Therefore, if the compound of the present invention is used, it is possible to perform an early diagnosis of a disease in which the amyloid β protein accumulates, such as Alzheimer's disease.

Further, the present invention provides a new drug development theory based on a keto-enol tautomerism. In addition, by utilizing the nature of the compound of the present invention in which the enol form and the keto form have different affinities, respectively, to an amyloid β peptide aggregate, which is a substance agent of Alzheimer's disease, the present invention provides a diagnostic imaging agent, an in-vitro diagnostic agent, and a diagnostic method for a disease in which the amyloid β peptide aggregate accumulates.

By adding the compound of the present invention to a body fluid such as serum, cerebrospinal fluid, or the like, the enol form binds to an amyloid β peptide aggregate contained in the body fluid. With respect to a compound that has ultraviolet absorption and visible absorption characteristics and has the keto-enol tautomerism, absorption spectra of the keto form and the enol form are different in general. Therefore, if the enol form binds to an amyloid β peptide aggregate, a color, emergence of an absorption spectrum, fluorescence coloring, and the like specific to the enol form are observed. Accordingly, amyloid β peptide aggregates contained in the body fluid can be measured, which enables use of the compound as an in-vitro diagnostic agent for Alzheimer's disease based on the keto-enol tautomerism. The in-vitro diagnostic agent of the present invention allows easier operations and shorter measurement time, than the conventional ELISA.

By radioactively labeling the compound of the present invention, the compound can be used as a diagnostic imaging agent, such as for PET and SPECT, for a disease in which an amyloid β peptide aggregate accumulates. The compound binds to the aggregate in the enol form and is released and excreted when the compound transforms into the keto-form. Therefore, the compound can be excreted from the body more promptly than a conventional reagent, and thus, adverse reactions can be reduced.

By causing an element, such as fluorine ($^{19}$F), that is appropriate for nuclear magnetic signal measurement, to bind to the compound of the present invention, the compound can be used as an MR diagnostic imaging agent for a disease in which an amyloid β peptide aggregate accumulates. Since the compound binds to the aggregate in the enol form and is released when the compound transforms into the keto form, a detection with a higher sensitivity than a conventional reagent is allowed.

DESCRIPTION OF EMBODIMENTS

Figure 1:
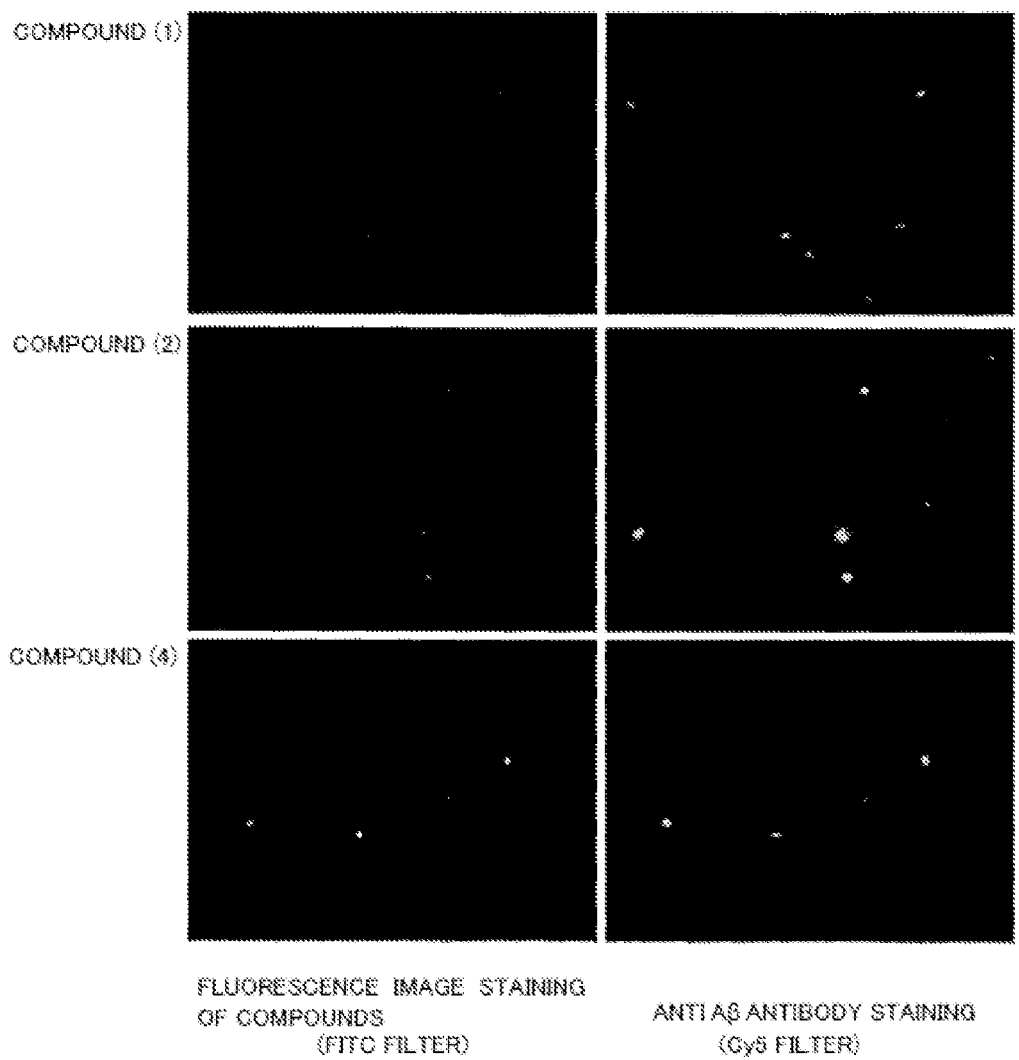
FIG. 1 shows stain images of slices of a cortex of a temporal lobe of a postmortem brain of an Alzheimer's disease patient.

Hereinafter, a compound, a diagnostic imaging agent, an in-vitro diagnostic agent, a diagnostic method, and the like of the present invention will be described in detail.

Examples of the compound according to the present invention specifically include those shown in Embodiments 1 and 2. Hereinafter, Embodiments 1 and 2 will be described.

Embodiment 1

Embodiment 1 of the present invention relates to a curcumin derivative or a salt thereof represented by formula (I):

[Chem. 3]

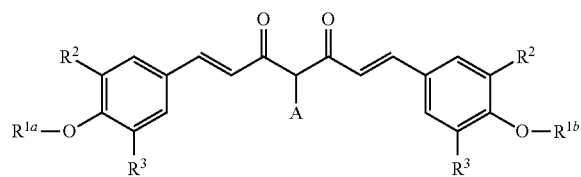

(wherein $R^{1a}$ and $R^{1b}$ are each independently a hydrogen atom, alkyl, acetyl, or methoxycarbonyl; $R^2$s are each independently a fluorine atom, $CHF_2$—, $CF_3$—, $CHF_2O$—, or $CF_3O$—; $R^3$s are each independently a hydrogen atom or a fluorine atom; A is alkyl, cyano, carboxyl, alkoxycarbonyl, or $R^4$—$(CH_2)_m$—; $R^4$ is hydroxy, carboxy, cyano, acetyloxy, alkoxycarbonyl, alkoxyalkoxy, hydroxyalkoxy, or $CONR^5R^6$; $R^5$ and $R^6$ are each independently a hydrogen atom or alkyl; and m is an integer from 1 to 5, preferably, from 1 to 3).

Further, Embodiment 1 of the present invention relates to a diagnostic imaging agent, for a disease in which an amyloid β protein accumulates, whose active component is a compound of formula (I) or a salt thereof.

Further, Embodiment 1 of the present invention relates to a staining agent, for an amyloid β protein in tissue such as brain or a senile plaque, whose active component is the compound of formula (I) or a salt thereof.

The alkyl group for $R^{1a}$, $R^{1b}$, A or $R^4$ may be any linear or branched $C_{1-6}$ alkyl, and preferably, a linear or branched $C_{1-3}$ alkyl group.

The alkyl group in the compound of formula (I) includes alkyl groups of alkoxycarbonyl, alkoxyalkoxy, and hydroxyalkoxy.

Specific examples of $C_{1-6}$ alkyl are methyl, ethyl, n-propyl, isopropyl, n-butyl, isobutyl, tert-butyl, n-pentyl, isopentyl, and hexyl.

Specific examples of $C_{1-3}$ alkyl are methyl, ethyl, n-propyl, and isopropyl.

The salt of the compound of formula (I) may be any salt that is allowable for medical use, and examples of the salt include alkali metal salts such as potassium salts and sodium salts; alkaline earth metal salts such as calcium salts; and organic amine salts such as triethanolamine salts and tris(hydroxymethyl)aminomethane salts. Some of these salts have water of crystallization.

The compound of formula (I) or the salt thereof can be produced by any of production methods [1] to [4].

Production Method [1]

The compound of formula (I) can be produced by: causing a compound of formula (II-a) to react with a compound of formula (III), to produce a compound of formula (IV), and then further causing the compound of formula (IV) to react with a compound of formula (II-b) under a similar reaction condition.

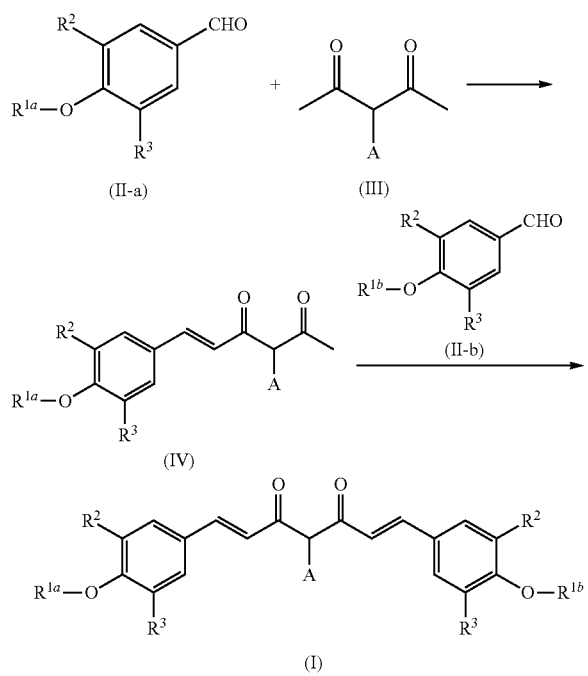

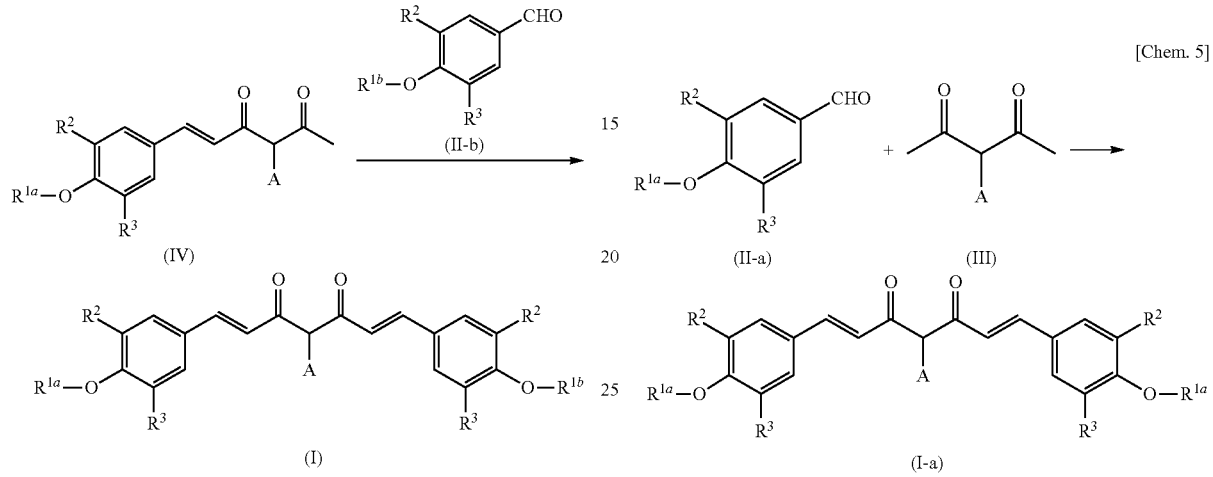

(wherein $R^{1a}$, $R^{1b}$, $R^2$, $R^3$, and A are as defined above.)

In production method [1], for performing an efficient reaction, it is desirable to perform the reaction under the presence of a boron compound and a base in a solvent. Examples of the boron compound that can be used in the present reaction include boric acid, diboron trioxide, tri-n-butyl borate, tri-tert-butyl borate, triethyl borate, trimethyl borate, triphenyl borate, tri-n-propyl borate, and a mixture of diboron trioxide and various borate esters. The use amount of the boric acid compound is from 0.5 equivalents to 6 equivalents relative to the compound of formula (II-a) or (IV).

Examples of the base include primary amines such as n-butylamine, sec-butylamine, tert-butylamine, n-propylamine, n-hexylamine, and cyclohexylamine; or secondary amines such as 1,2,3,4-tetrahydroquinoline. Preferably, the use amount of the base is from a catalyst quantity to about 1 equivalent relative to compound (III).

Examples of the solvent include aromatic hydrocarbons such as benzene, toluene, and xylene; aliphatic hydrocarbons such as pentane, hexane, heptane, petroleum ether, ligroin, and petroleum benzin; ethers such as diethyl ether, diisopropyl ether, dibutyl ether, tetrahydrofuran, and dioxane; esters such as ethyl acetate, methyl acetate, and methyl propionate; acid amides such as dimethylformamide and dimethylacetamide; sulfoxides such as dimethyl sulfoxide; phosphate amides such as hexamethylphosphoramide; and a mixed solvent of these.

Desirably, in the present reaction, the compound of formula (II-a) is used relative to the compound of formula (III) at a ratio of 1 mol:1 mol, respectively, and the compound of formula (II-b) is used relative to the compound of formula (IV) at a ratio of 1 mol:1 mol, respectively. The reaction temperature is 0 to 150° C., and desirably, 0 to 100° C., and the reaction time is about 0.5 to 24 hours.

After the above reaction, it is necessary to perform acid treatment, in order to decompose boron complexes of the compound of formula (IV) or (I). Examples of the acid used for the treatment include mineral acids such as hydrochloric acid, and organic acids such as acetic acid.

Production Method [2]

With respect to formula (I), a compound of formula (I-a), in which substituents $R^{1a}$s, $R^2$s, and $R^3$s in formula (I) are present in bilateral symmetry, can be produced by causing 2 mol of the compound of formula (II-a) to react with 1 mol of the compound of formula (III) under a similar reaction condition to that for production method [1].

(wherein $R^{1a}$, $R^2$, $R^3$, and A are as defined above except that $R^2$s and $R^3$s are positioned in bilateral symmetry.)

Production Method [3]

With respect to formula (I), a compound of formula (I-b), in which substituent A in formula (I) is —COOH or —$(CH_2)_m$—COOH, can be produced by causing a compound of formula (I-c) to react with an acid or a base.

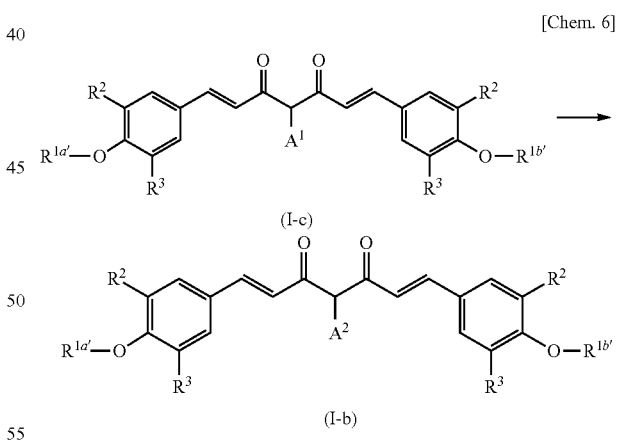

(wherein $A^1$ is alkoxycarbonyl or —$(CH_2)_m$—$COOR^4$, $A^2$ is —COOH or —$(CH_2)_m$—COOH, $R^{1a'}$ and $R^{1b'}$ are each independently a hydrogen atom or alkyl, and $R^2$, $R^3$, $R^4$, and m are as defined above.)

The alkyl group of $R^{1a'}$ or $R^{1b'}$ may be any linear or branched $C_{1-6}$ alkyl, and preferably, a linear or branched $C_{1-3}$ alkyl group.

In the case of a reaction with an acid, examples of the acid that can be used include: mineral acids such as sulfuric acid, hydrochloric acid, hydrofluoric acid, and hydrobromic acid; and organic strong acids such as trifluoroacetic acid.

Although the use amount of the acid is not specifically limited, it is desirably 0.1 to 10 equivalents relative to the compound of formula (I-c). The reaction temperature is −10 to 100° C., and desirably, −10 to 50° C., and the reaction time is about 0.5 to 24 hours.

When a base is used, examples of the base that can be used include alkali metals such as potassium hydroxide and sodium hydroxide. The use amount of the base is 3 to 10 equivalents relative to the compound of formula (I-c), the reaction temperature is 0 to 100° C., and the reaction time is about 0.1 to 24 hours.

Desirably, the present reaction is performed under the presence of a solvent, and examples of the solvent include ethers such as tetrahydrofuran, and dioxane; alcohols such as methanol, ethanol, propyl alcohol, and isopropyl alcohol; and water. In the case of the reaction with the acid, the acid itself can be used as the solvent.

Production Method [4]

With respect to formula (I), a compound of formula (I-d), in which both of $R^{1a}$ and $R^{1b}$ in formula (I) are $CH_3C(=O)-$ or $CH_3C(=O)-$, can be produced by causing the compound of formula (I-e) to react with a compound of formula (V) under the presence of a solvent in general.

[Chem. 7]

(wherein $R^5$ is $CH_3-$ or $CH_3O-$, X is a halogen atom, and A, $R^2$, and $R^3$ are as defined above.)

Here, the halogen atom denotes fluorine, chlorine, bromine, and iodine.

Desirably, in the present reaction, the compound of formula (V) is used relative to the compound of formula (I-e) at a ratio of about 3 mol:1 mol, respectively. The reaction temperature is, in general, 0 to 150° C. and desirably, 0 to 100° C. The reaction time is about 0.5 to 24 hours.

For performing an efficient reaction, it is desirable to perform the reaction under the presence of a base. Examples of the base that can be used include tertiary amines such as triethylamine and tributylamine; and pyridine. The use amount of the base is from a catalyst quantity to 2 to 4 mol relative to the compound (1-e).

The present reaction can be performed under the presence of a solvent. Examples of the solvent include: aromatic hydrocarbons such as benzene, toluene, and xylene; aliphatic hydrocarbons such as pentane, hexane, heptane, petroleum ether, ligroin, and petroleum benzin; ethers such as diethyl ether, diisopropyl ether, dibutyl ether, tetrahydrofuran, and dioxane; esters such as ethyl acetate, methyl acetate, and methyl propionate; acid amides such as dimethylformamide and dimethylacetamide; sulfoxides such as dimethyl sulfoxide; phosphate amides such as hexamethylphosphoramide; and a mixed solvent of these.

The compound of formula (I) obtained by production methods [1] to [4] described above and a method associated therewith can be isolated and purified by a known means, such as, for example, concentration, vacuum concentration, distillation, fractional distillation, re-dissolution, solvent extraction, crystallization, recrystallization, and chromatography.

In a case where the compound of formula (I) is obtained as a free form, it is possible to form a salt by an ordinary method.

Table 1 shows examples of the compound of formula (I).

TABLE 1

| Compound | Structure | Physical property |
| --- | --- | --- |
| Compound 1 | 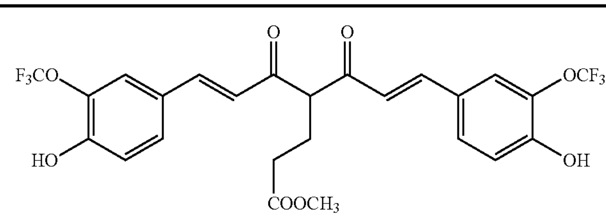 | mp. 142-143° C. |
| Compound 2 | 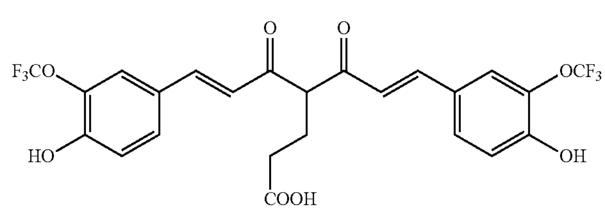 [SMILES: O=C(O)CCC(C(=O)/C=C/c1ccc(O)c(OC(F)(F)F)c1)C(=O)/C=C/c1ccc(O)c(OC(F)(F)F)c1] | mp. 150-151° C. |

TABLE 1-continued

| Compound | Structure | Physical property |
|---|---|---|
| Compound 3 | 3-F, 4-OCH₃ aryl — CH=CH—C(O)—CH(CH₂CH₂COOCH₃)—C(O)—CH=CH — 3-F, 4-OCH₃ aryl | mp. 170-171° C. |
| Compound 4 | 3-F, 4-OCH₃ aryl — CH=CH—C(O)—CH(CH₂CH₂COOH)—C(O)—CH=CH — 3-F, 4-OCH₃ aryl | mp. 171-172° C. |
| Compound 5 | 3-OCF₃, 4-OH aryl — CH=CH—C(O)—CH(CH₂COOCH₃)—C(O)—CH=CH — 3-OCF₃, 4-OH aryl | mp. 140-141° C. |
| Compound 6 | 3-OCF₃, 4-OH aryl — CH=CH—C(O)—CH(CH₂CH₂CH₂COOCH₃)—C(O)—CH=CH — 3-OCF₃, 4-OH aryl | mp. 147-148° C. |
| Compound 7 | 3-OCF₃, 4-OH aryl — CH=CH—C(O)—CH(COOCH₂CH₃)—C(O)—CH=CH — 3-OCF₃, 4-OH aryl | mp. 179-180° C. |
| Compound 8 | 3-OCF₃, 4-OH aryl — CH=CH—C(O)—CH(CH₂CH₂COOCH₂CH₃)—C(O)—CH=CH — 3-OCF₃, 4-OH aryl | mp. 155-156° C. |
| Compound 9 | 3-OCF₃, 4-OH aryl — CH=CH—C(O)—CH(CH₂CH₂COOC(CH₃)₃)—C(O)—CH=CH — 3-OCF₃, 4-OH aryl | mp. 175° C. |
| Compound 10 | 3-OCF₃, 4-OH aryl — CH=CH—C(O)—CH(CH₂CH₂COOCH(CH₃)₂)—C(O)—CH=CH — 3-OCF₃, 4-OH aryl | mp. 191° C. |

TABLE 1-continued

| Compound | Structure | Physical property |
|---|---|---|
| Compound 11 | 3,5-difluoro-4-hydroxyphenyl bis-enone with CH₂CH₂COOCH₃ substituent at central carbon | mp. 178-179° C. |
| Compound 12 | 3-fluoro-4-methoxyphenyl bis-enone with CH₂CH₂COONa substituent at central carbon | mp. >200° C. |
| Compound 13 | 3-trifluoromethoxy-4-hydroxyphenyl bis-enone with CH₂CH₂CH₂OCOCH₃ substituent at central carbon | mp. 130-131° C. |
| Compound 14 | 3-trifluoromethyl-4-hydroxyphenyl bis-enone with CH₂CH₂COOCH₃ substituent at central carbon | mp. 183° C. |
| Compound 15 | 3-trifluoromethoxy-4-hydroxyphenyl bis-enone with CH₂CH₂CN substituent at central carbon | mp. 134-135° C. |
| Compound 16 | 3-trifluoromethoxy-4-hydroxyphenyl bis-enone with CH₃ substituent at central carbon | mp. 178-179° C. |
| Compound 17 | 3-trifluoromethoxy-4-acetoxyphenyl bis-enone with CH₂CH₂COOCH₃ substituent at central carbon | mp. 149-150° C. |

TABLE 1-continued

| Compound | Structure | Physical property |
|---|---|---|
| Compound 18 | F$_3$CO, HO, (structure), COOCH$_3$, OCF$_3$, OCOCH$_3$ | mp. 124-126° C. |
| Compound 19 | F$_3$CO, NaO, (structure), COOCH$_3$, OCF$_3$, ONa | mp. >200° C. |
| Compound 20 | F$_3$CO, HO, (structure), OCH$_2$OCH$_3$, OCF$_3$, OH | Oily matter |
| Compound 21 | F$_3$CO, HO, (structure), CON(CH$_3$)$_2$, OCF$_3$, OH | mp. 192-193° C. |
| Compound 22 | F$_3$CO, HO, (structure), OCH$_2$CH$_2$OH, OCF$_3$, OH | mp. 112-114° C. |

The compound of formula (I) and a salt thereof can be used as a diagnostic imaging agent for a disease in which an amyloid β protein accumulates. Also, the compound of formula (I) and a salt thereof can be used as a staining agent for the amyloid β protein in tissue such as brain and a senile plaque.

Preferred embodiments of the present invention are as follows.

(1) A diagnostic imaging agent, for a disease in which an amyloid β protein accumulates, whose active component is the compound of formula (I) or a salt thereof.

(2) The diagnostic imaging agent according to (1), wherein the disease in which the amyloid β protein accumulates is Alzheimer's disease.

(3) The diagnostic imaging agent according to (1) or (2), being an MRI contrast medium for intracerebral amyloids.

(4) A staining agent, for an amyloid β protein in tissue such as brain or a senile plaque, whose active component is the compound of formula (I) or the salt thereof.

(5) The staining agent according to (4), being a fluorescent staining agent for the amyloid β protein.

(6) A diagnostic method, using the diagnostic imaging agent according to (1), for a disease in which a β-sheet structure of a protein is a cause of the disease or a part of the cause of the disease.

(7) A method for staining an amyloid β protein in tissue or a senile plaque by using the staining agent according to (4).

Many compounds categorized as the compound of formula (I) are hydrophobic compounds and have low solubility in water. As a compound to be administered to a living body, the compound preferably has a high solubility in water, and among compounds categorized as the compound of formula (I), a compound that has a salt is more desirable.

In a case where the compound of formula (I) or the salt thereof is used as a diagnostic imaging agent, it is possible to specifically detect an intracerebral senile plaque by means of the compound. In particular, in a case where an amyloid β protein is noninvasively detected by use of $^{19}$F-MRI, the detectivity depends on the number of fluorine atoms, and it is desirable that the number of F atoms is large.

In a case where the compound of formula (I) or the salt thereof is used as a diagnostic imaging agent, the compound may be administered locally or systemically. The administration method is not specifically limited, and the compound is administered orally or parenterally. The parenteral administration route may be an injection, a drip infusion, or the like under the skin or into the abdominal cavity, vein, artery or spinal fluid.

The diagnostic imaging agent comprising the compound of formula (I) or the salt thereof is in a form appropriate for administration to a human and allowable for medical use, and contains a physiologically allowable additive. To such a composition, there may be added, as appropriate, a diluent, a buffer, a solubilizing agent (for example, cyclodextrin, polyethylene glycol, or a surfactant such as Tween, Pluronic, Cremophor, or a phospholipid), a soothing agent, and the like that are allowable for medical use. Moreover, the composition may further contain, as necessary, a component such as a solvent, a stabilizing agent, or an antioxidant (for example, ascorbic acid) that is allowable for medical use. The dose of the compound of the present invention is selected, as appropriate, in accordance with the usage, the age, sex and other conditions of the patient, and the degree of the progress of the disease.

Examples of the disease in which an amyloid β protein accumulates include Down's syndrome in addition to Alzheimer's disease. Examples of the disease in which the β-sheet structure of a protein is a cause of the disease or a part of the cause of the disease include frontotemporal dementia, Pick's disease, progressive supranuclear palsy PSP), prion disease, and the like, in addition to Alzheimer's disease and Down's syndrome.

Embodiment 2

A diagnostic imaging agent according to Embodiment 2 of the present invention is directed to a diagnostic imaging agent for diagnosing a disease in which an amyloid β peptide aggregate accumulates, the diagnostic imaging agent comprising a compound having a 1,3-dicarbonyl structure, wherein the compound exists in a keto form and an enol form, and the keto form and the enol form have different affinities, respectively, to the amyloid β peptide aggregate.

An in-vitro diagnostic agent according to Embodiment 2 of the present invention is directed to an in-vitro diagnostic agent for diagnosing a disease in which an amyloid β peptide aggregate accumulates, the in-vitro diagnostic agent comprising a compound having a 1,3-dicarbonyl structure, wherein the compound exists in a keto form and an enol form, and the enol form has a higher affinity to the amyloid β peptide aggregate than the keto form.

In the present invention, an amyloid β peptide denotes a peptide that is composed of 38 to 43 amino acids and that is generated from an amyloid precursor protein as a result of an action by a protease, and an amyloid β peptide aggregate denotes a tetramer or greater.

Hereinafter, description will be given of a compound used in the diagnostic agent (diagnostic imaging agent and in-vitro diagnostic agent) according to Embodiment 2 of the present invention.

Compound Used as Diagnostic Agent

The compound Used as the diagnostic agent of the present invention is a compound having a 1,3-dicarbonyl structure, and existing in a keto form and an enol form.

Here, the compound having the 1,3-dicarbonyl structure is a compound having a structure below.

[Chem. 8]

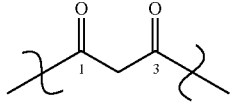

In the compound having the 1,3-dicarbonyl structure of the present invention, the keto form denotes a compound which has ketones at both the first position and the third position, respectively, and the enol form denotes a compound which is enolized at either one of the first position and the third position.

In the present invention, the compound having the 1,3-dicarbonyl structure includes a compound that is a compound of the enol form but can have the 1,3-dicarbonyl structure.

The present invention is a diagnostic agent for a disease in which an amyloid β peptide aggregate accumulates, the diagnostic agent being based on a new theory utilizing a keto-enol tautomerism. The compound having the 1,3-dicarbonyl structure of the present invention used as a diagnostic imaging agent is a compound having a nature that the keto form and the enol form have different affinities, respectively, to an amyloid β peptide aggregate, which is a causative substance of Alzheimer's disease, and a nature that the enol form has a higher affinity to the amyloid β peptide aggregate than the keto form. Similarly, the compound having the 1,3-dicarbonyl structure of the present invention used as an in-vitro diagnostic agent is a compound having a nature that the enol form has a higher affinity to an amyloid β peptide aggregate than the keto form.

It is desirable that the compound having the 1,3-dicarbonyl structure exists mainly as the keto form in water with a high polarity and as the enol form in an organic solvent with a low polarity. To this end, it is preferable that one substituent, in particular, an alkyl group, is introduced at the second position of the 1,3-dicarbonyl structure. In such a case, the alkyl group may be one that is substituted. In a case where the compound having the 1,3-dicarbonyl structure of the present invention contains an asymmetric carbon, both of optical isomers separated by an ordinary method and racemes are included in the compound of the present invention.

In a case where the compound having the 1,3-dicarbonyl structure is used as a diagnostic imaging agent, it is preferable that the compound is labeled. A label is a substance that enables detection of a compound, and examples thereof include radioactive isotopes, photolabels including fluorescence, MR signals, and the like. The compound having the 1,3-dicarbonyl structure of the present invention can be used as: an MR diagnostic imaging agent when an atom, such as $^{19}F$, that is appropriate for nuclear magnetic signal measurement, is used as the label; a PET diagnostic imaging agent when a positron emitting nuclide is used as the label; and a single-photon emission computed tomography (SPECT) diagnostic imaging agent when a γ ray emitting nuclide is used as the label. Each of the atom and the nuclides used as the label may be bound to any position of the compound having the 1,3-dicarbonyl structure of the present invention as long as they do not cause the binding strength to the amyloid β peptide aggregate to be lost. The dose of the compound having the 1,3-dicarbonyl structure of the present invention may be any quantity that provides a sufficient quantity of the bound compound to an extent that allows diagnostic imaging.

The compound having the 1,3-dicarbonyl structure of the present invention has the keto-enol tautomerism, the enol form is contained in a water solution by 0.01 to 50%, preferably, 0.01 to 10%, and more preferably, 0.01 to 5%. For measurement of the proportion of the enol form, a water solution (pH: 7.5, temperature: 20° C.) is used which is obtained by dissolving, in a phosphate buffer, the compound having the 1,3-dicarbonyl structure of the present invention at a concentration of 0.01 to 5 mM. The proportion of the enol form can be obtained by measuring, by NMR, the peak area intensity of $^1H$, $^{19}F$, or $^{13}C$, and preferably $^{19}F$, for each of the keto form and the enol form in the water solution. A radioactively labeled material would cause less adverse reaction such as radiation injury if it is removed in a short period of time. Therefore, it is desirable that after the compound binds to a senile plaque and the imaging thereof is finished, the compound is released from the senile plaque to be promptly excreted. To this end, it is desirable that the proportion of the keto form is high in the water solution, and in particular, 70% or more. On the other hand, it is desirable that in a state where the compound is bound to an amyloid β peptide aggregate, the proportion of the enol form is high, and in particular, 70% or more.

Desirably, with respect to the compound having the 1,3-dicarbonyl structure of the present invention, the affinity of the enol form to an amyloid β peptide aggregate is 10 times or more the affinity of the keto form town amyloid β peptide aggregate, in terms of the $IC_{50}$ value of a fluorescence inhibition test.

An example of the compound having the 1,3-dicarbonyl structure of the present invention includes the compound below.

Formula (i):

[Chem. 9]

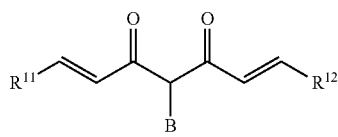

wherein $R^{11}$ and $R^{12}$ are each independently an aryl group or a heteroaryl group that may be substituted, and B is hydrogen or an alkyl group that may be substituted. B is preferably an alkyl group that may be substituted. In a case where this compound is used as a diagnostic imaging agent, the label defined above is preferably introduced.

The terms concerning the compound of formula (I) will be described below.

"Aryl group" denotes a monocyclic or a polycyclic group composed of 5- or 6-membered aromatic hydrocarbon ring(s), and specific examples include phenyl, naphthyl, fluorenyl, anthryl, biphenylyl, tetrahydronaphthyl, chromanyl, 2,3-dihydro-1,4-dioxanaphthalenyl, indanyl, and phenanthryl.

"Heteroaryl group" denotes a monocyclic or polycyclic group composed of 5- or 6-membered aromatic ring(s) and containing 1 to 3 heteroatoms selected from the group consisting of N, O, and S. In the case of the polycyclic group, it is sufficient that at least one ring is an aromatic ring. Specific examples include furyl, thienyl, pyrrolyl, imidazolyl, pyrazolyl, oxazolyl, thiazolyl, isoxazolyl, isothiazolyl, pyridyl, pyrazinyl, pyrimidinyl, pyridazinyl, indolyl, quinolyl, isoquinolyl, benzo[b]thienyl, and benzimidazolyl.

"Alkyl group" may be any linear $C_{1-5}$ alkyl group, and specific examples thereof include methyl, ethyl, n-propyl, n-butyl, and n-pentyl, and preferably, a linear $C_{1-3}$ alkyl group.

"Aryl group or heteroaryl group that may be substituted" denotes an aryl group and a heteroaryl group that may be substituted with 1 to 4 atoms or groups that are selected from the group consisting of hydroxy, $C_{1-6}$ alkyl, methoxy, acetoxy, methoxycarbonyloxy, fluorine, $CHF_2-CF_3-$, $CHF_2O-CF_3O-$, methylamino, $CH_3OOCCH_2O-$, and $HOOCCH_2O-$. Here, a compound containing a fluorine atom is equivalent to one into which the label has been introduced, and therefore, can be used as an MR diagnostic imaging agent.

"Alkyl group that may be substituted" denotes an alkyl group that may be substituted with hydroxy, carboxyl, cyano, acetyloxy, trifluoroethoxy, $C_{1-6}$ alkoxycarbonyl, alkoxyalkoxy, hydroxyalkoxy or $CONR^{13}R^{14}$ ($R^{13}$ and $R^{14}$ are each independently a hydrogen atom or alkyl). Here, the alkyl group in alkoxyalkoxy, hydroxyalkoxy and $CONR^{13}R^{14}$ may be any linear or branched $C_{1-6}$ alkyl, and preferably, a linear or branched $C_{1-3}$ alkyl group.

The compound having the 1,3-dicarbonyl structure of the present invention may be a salt, such as the salt of the compound of formula (I).

The compound of formula (i) or a salt thereof can be produced by a method according to either of production methods [5] and [6] below.

Production Method [5]

The compound of formula (i) can be produced by causing a compound of formula (ii-a) to react with a compound of formula (iii) to produce a compound of formula (iv), and then further causing the compound of formula (iv) to react with a compound of formula (ii-b) under a similar reaction condition.

[Chem. 10]

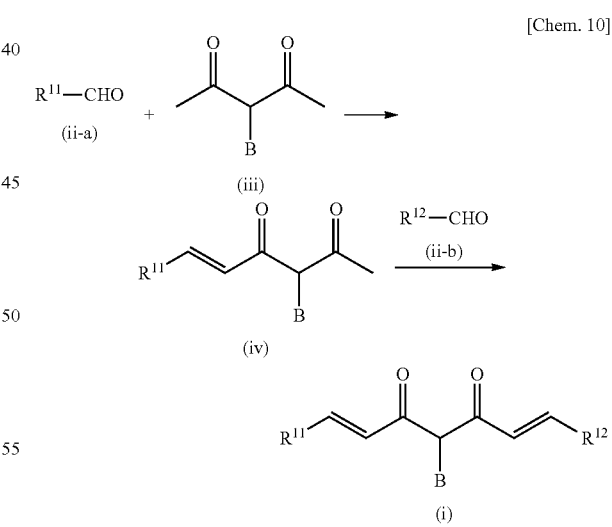

(wherein $R^{11}$, $R^{12}$, and B are as defined above.)

In production method [5], for performing an efficient reaction, it is desirable to perform the reaction under the presence of a boron compound and a base in a solvent. As the boron compound, chlorine, and the solvent in the present reaction, those used in production method [1] can be used. The use amount of a boric acid compound is 0.5 equivalents to 6 equivalents relative to the compound of formula (iii) or (iv).

The use amount of the base is preferably from a catalyst quantity to about 1 equivalent relative to the compound (iii).

Desirably, in the present reaction, the compound of formula (ii-a) is used relative to the compound of formula (iii) at a ratio of 1 mol:1 mol, respectively, and the compound of formula (ii-b) is used relative to the compound of formula (iv) at a ratio of 1 mol:1 mol. The reaction temperature is 0 to 150° C., and desirably, 0 to 100° C., and the reaction time is about 0.5 to 24 hours.

After the above reaction, it is necessary to perform acid treatment, in order to decompose boron complexes of the compound of formula (iv) or (i). Examples of the acid used for the treatment include mineral acids such as hydrochloric acid, and organic acids such as acetic acid.

Production Method [6]

With respect to formula (i), a compound of formula (i-a), in which substituents $R^{11}$ and $R^{12}$ in formula (i) are the same with each other, can be produced by causing 2 mol of the compound of formula (ii-a) to react with 1 mol of the compound of formula (iii) under a similar reaction condition to that for production method [5].

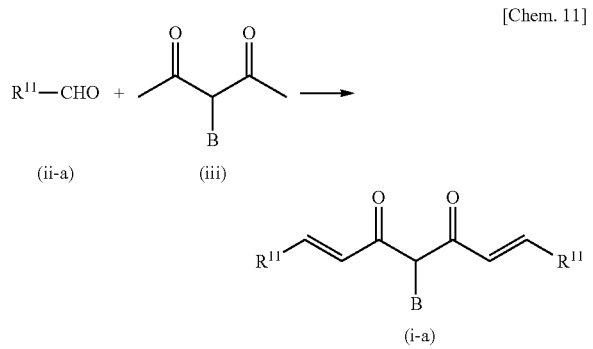

[Chem. 11]

(wherein $R^{11}$ and B are as defined above.)

The compound of formula (i) obtained by production methods [5] to [6] described above and a method associated therewith can be isolated and purified by a known means, such as, for example, concentration, vacuum concentration, distillation, fractional distillation, re-dissolution, solvent extraction, crystallization, recrystallization, and chromatography.

In a case where the compound of formula (I) is obtained as a free form, it is possible to form a salt by an ordinary method.

Diagnostic Imaging Agent

The compound having the 1,3-dicarbonyl structure of the present invention can be used as a diagnostic imaging agent for a disease in which an amyloid β peptide aggregate accumulates. The compound having the 1,3-dicarbonyl structure of the present invention can be used as a $^{19}F$-MRI contrast medium, that is, an MR diagnostic imaging agent, by causing the compound to contain many $^{19}F$ atoms. Since an atom, other than $^{19}F$, that is appropriate for measurement of nuclear magnetic resonance signals, can be similarly used as an MR diagnostic imaging agent, the type of MRI is not limited to $^{19}F$-MRI. The position in the compound having the 1,3-dicarbonyl structure of the present invention, at which position the atom appropriate for the nuclear magnetic signal measurement is to be introduced, may be any position, and is not limited to a particular position.

The compound having the 1,3-dicarbonyl structure of the present invention can be used as a PET diagnostic imaging agent, by causing the compound to contain $^{11}C$, $^{13}N$, $^{15}O$, $^{18}F$, $^{62}Cu$, $^{68}Ga$, $^{76}Br$, or the like, which is a positron emitting nuclide. Among these, $^{18}F$ is preferable in particular. The compound having the 1,3-dicarbonyl structure of the present invention can be used as a SPECT diagnostic imaging agent, by causing the compound to contain $^{99m}Tc$, $^{111}In$, $^{67}Ga$, $^{201}Tl$, $^{123}I$, $^{133}Xe$, or the like, which is a γ ray emitting nuclide. The position at which the compound having the 1,3-dicarbonyl structure of the present invention is labeled with the positron emitting nuclide or the γ ray emitting nuclide may be any position in the compound. Alternatively, hydrogen on the ring may be substituted with a positron emitting nuclide or a γ ray emitting nuclide.

In general, the above nuclides are generated by an apparatus called cyclotron or generator. A person skilled in the art can select, as appropriate, a generation method and a generation apparatus that are appropriate for the nuclide to be generated. Production methods of a compound labeled by the radionuclides are well known in the field. Representative methods are a chemical synthesis method, an isotope exchange method, and a biosynthetic method.

In a case where the compound having the 1,3-dicarbonyl structure of the present invention is used as a diagnostic imaging agent, it is possible to specifically detect an intracerebral senile plaque by the compound. In particular, in a case where an amyloid β peptide aggregate is noninvasively detected by use of $^{19}F$-MRI in an MR diagnostic imaging method, the detectivity depends on the number of fluorine atoms, and it is desirable that the number of F atoms is larger.

In a case where the compound having the 1,3-dicarbonyl structure of the present invention is used as a diagnostic imaging agent, the compound may be administered locally or systemically. The administration method is not specifically limited, and the compound is administered orally or parenterally. An example of the parenteral administration route may be an injection, a drip infusion, or the like under the skin or into the abdominal cavity, vein, artery or spinal fluid.

The time period during which the diagnostic imaging agent of the present invention administered to a human reaches the part where the amyloid β peptide aggregate is accumulated, thereby enabling the diagnosis, is 0.5 to 6 hours, preferably, 0.5 to 2 hours, after the administration.

The diagnostic imaging agent of the present invention is in a form appropriate for administration to a human and allowable for medical use, and contains an additive that is physiologically allowable. To such a diagnostic imaging agent, there may be added, as appropriate, a diluent, a buffer, a solubilizing agent (for example, cyclodextrin, polyethylene glycol, or a surfactant such as Pluronic, Tween, Cremophor, or a phospholipid), a soothing agent, and the like, that are allowable for medical use. Moreover, the diagnostic imaging agent may further contain, as necessary, a component such as a solvent, a stabilizing agent, or an antioxidant (for example, ascorbic acid) that is allowable for medical use. The dose of the compound having the 1,3-dicarbonyl structure of the present invention may be any quantity that provides a sufficient quantity of the bound compound to an extent that allows detection of the amyloid β peptide aggregate, and is selected, as appropriate, in accordance with the usage, the age, sex and other conditions of the patient, and the degree of the progress of the disease.

Examples of the disease in which the amyloid β peptide aggregate accumulates include Down's syndrome in addition to Alzheimer's disease. Alzheimer's disease in the present invention includes, in addition to Alzheimer's disease of a human, Alzheimer's disease of an Alzheimer's disease model animal.

In-Vitro Diagnostic Agent

The compound having the 1,3-dicarbonyl structure of the present invention can be used as an in-vitro diagnostic agent for a disease in which an amyloid β peptide aggregate accumulates.

The use amount in a case where the compound having the 1,3-dicarbonyl structure of the present invention is used as the in-vitro diagnostic agent may be any quantity that provides a sufficient quantity of the bound compound to an extent that allows determination of the presence of the amyloid β peptide aggregate, and is selected as appropriate based on conditions of the kind of the sample, concentration, and the like.

The in-vitro diagnostic agent of the present invention allows determination of the presence of an amyloid β peptide aggregate, in 5 to 720 minutes, and in particular, 15 to 60 minutes, after the in-vitro diagnostic agent is used onto a sample.

In a case where the compound having the 1,3-dicarbonyl structure of the present invention is used as the in-vitro diagnostic agent, the enol form of the compound of the present invention binds to an amyloid β peptide aggregate contained in the body fluid, and a color, emergence of an absorption spectrum, fluorescence coloring, and the like that are specific to the enol form are observed. Accordingly, by detecting the change of the absorbance and by measuring the fluorescence, it is possible to measure the amyloid β peptide aggregate contained in the body fluid. Although depending on the kind of the compound to be used as the in-vitro diagnostic agent, examples of the absorption wavelength used in the detection are 400 to 600 nm; and for the fluorescence detection, examples of the excitation wavelength are 400 to 450 nm, and examples of the fluorescence wavelength are 500 to 600 nm.

Examples of the sample for the in-vitro diagnostic agent of the present invention include blood, cerebrospinal fluid, and in addition, body fluids such as tears, saliva, nasal discharge, and urine.

The in-vitro diagnostic agent of the present invention may contain other additives to an extent that does not inhibit the function of the in-vitro diagnostic agent.

Examples of the disease in which an amyloid β peptide aggregate accumulates include those described above.

Diagnostic Method

The present invention provides a diagnostic method, for a disease in which an amyloid β peptide aggregate accumulates, which uses the above diagnostic imaging agent. The diagnostic method of the present invention for a disease in which an amyloid β peptide aggregate accumulates is realized by administrating into blood of a subject the diagnostic imaging agent comprising the compound having the 1,3-dicarbonyl structure of the present invention, and by detecting the compound in the brain.

The present invention also provides a diagnostic method, for a disease in which an amyloid β peptide aggregate accumulates, which uses the above in-vitro diagnostic agent. The diagnostic method of the present invention for a disease in which an amyloid β peptide aggregate accumulates is realized by using onto a sample collected from a subject the in-vitro diagnostic agent comprising the compound having the 1,3-dicarbonyl structure of the present invention, and by detecting a change in the absorbance of the compound or by measuring the fluorescence.

With respect to the administration method, the dose, and the like of the diagnostic imaging agent and the usage, the use amount, and the like of the in-vitro diagnostic agent to be used in these diagnostic methods, those described above are applied.

Examples of the disease in which an amyloid β peptide accumulates include those described above.

EXAMPLES

Next, synthetic examples and test examples relating to the present invention will be described. However, the present invention is not limited thereto.

Synthetic Example 1

Synthesis of 1,7-bis(4'-hydroxy-3'-trifluoromethoxyphenyl)-4-methoxycarbonylethyl-1,6-heptadiene-3,5-dione (compound 1)

After an ethyl acetate (10 mL) solution containing methyl 4-acetyl-5-oxohexanoate 0.93 g (5 mmol) and diboron trioxide 0.28 g (4 mmol) was heated for 30 minutes to 40° C., 4-hydroxy-3-(trifluoromethoxy)benzaldehyde 2.06 g (10 mmol) and tri-n-butyl borate 2.7 mL (10 mmol) were added to the solution, and the resultant solution was continued to be heated at the same temperature for another 30 minutes. Then, an ethyl acetate (1 mL) solution containing n-butylamine 0.5 mL (5 mmol) was added, and the resultant solution was heated at 40° C. for 3 hours. After the reaction solution was cooled to room temperature, 1M-hydrochloric acid (15 mL) was added, and the resultant solution was agitated vigorously for 10 minutes. Ethyl acetate (100 mL) was added to the reaction solution. The organic layer was washed with 0.5M-hydrochloric acid, further washed with a saturated sodium bicarbonate water solution and with a saturated saline solution, and then dried with magnesium sulfate. Then, the solvent was removed by a rotary evaporator. A small quantity of dichloromethane was added to a substance obtained by purifying the residue by silica gel column chromatography (eluant: ethyl acetate:n-hexane=1:2), and the resultant mixture was left to stand at room temperature. Then, 1.51 g of 1,7-bis(4'-hydroxy-3'-trifluoromethoxyphenyl)-4-methoxycarbonylethyl-1,6-heptadiene-3,5-dione having a melting point of 142 to 143° C. was obtained.

$^1$HNMR ($d_6$DMSO): δ2.0 to 3.2 (4H), δ3.60 (s, 1.4H), δ3.64 (s, 1.6H), δ4.65 (t, J=7.0 Hz, 0.55H), δ7.03 (d, J=16.2 Hz, 1.1H), δ7.10 (d, J=8.6 Hz, 1.1H), δ7.12 (d, J=8.6 Hz, 0.9H), δ7.25 (d, J=16.2 Hz, 0.9H), δ7.6 to 7.75 (arom.H, 4H), δ7.81 (d, J=16.2 Hz, 2H), δ10.90 (br.s, 2H), δ17.90 (s, 0.45H)

$^{19}$FNMR ($d_6$ DMSO): δ-58.09 (s), δ-57.96 (s)

Synthetic Example 2

Synthesis of 1,7-bis(4'-hydroxy-3'-trifluoromethoxyphenyl)-4-carboxylethyl-1,6-heptadiene-3,5-dione (compound 2)

A quantity of 562 mg (1.0 mmol) of 1,7-bis(4'-hydroxy-3'-trifluoromethoxyphenyl)-4-methoxycarbonylethyl-1,6-heptadiene-3,5-dione obtained in synthetic example 1 was added to 30 mL of a 0.1M-sodium hydroxide aqueous solution, and then the resultant solution was agitated at room temperature for 4 hours. Then, the resultant solution was adjusted to pH2 by using 6M-hydrochloric acid, then was subjected to extraction with diethyl ether. After the extract was washed with water once, and was subjected to extraction 6 times with a saturated sodium bicarbonate water solution. The extract was washed with diethyl ether, and adjusted to pH2 with 6M-hydrochloric acid, and was subjected to extraction with diethyl ether. The extract was cleaned with a saturated saline solution, and then was dried with magnesium sulfate. Then, a small quantity of dichloromethane was added to the residue obtained by removing the solvent by a rotary evaporator, and the resultant mixture was left to stand at room temperature. Then, 346 mg of 1,7-bis(4'-hydroxy-3'-trifluoromethoxyphenyl)-4-carboxylethyl-1,6-heptadiene-3,5-dione having a melting point of 150 to 151° C. was obtained.

$^1$HNMR ($d_6$ DMSO): δ1.7 to 3.1 (4H), δ4.65 (t, J=7.0 Hz, 0.6H), δ7.03 (d, J=16.2 Hz, 1.2H), δ7.1 to 7.2 (2H), δ7.28 (d, J=16.2 Hz, 0.8H), δ7.5 to 7.9 (6H), δ11.1 (br.s, 2H), δ17.88 (s, 0.4H)

$^{19}$FNMR ($d_6$ DMSO): δ-57.97 (s), δ-57.84 (s)

Synthetic Example 3

Synthesis of 1,7-bis(4'-hydroxy-3'-trifluoromethoxyphenyl)-4-acetoxypropyl-1,6-heptadiene-3,5-dione (compound 13)

After an ethyl acetate (5 mL) solution containing 4-acetyl-5-oxohexyl acetate 180 mg (0.9 mmol) and diboron trioxide 63 mg (0.9 mmol) was heated for 30 minutes to 40° C., 4-hydroxy-3-(trifluoromethoxy)benzaldehyde 370 mg (1.8 mmol) and tri-n-butyl borate 828 mg (3.6 mmol) were added to the solution, and the resultant solution was continued to be heated at the same temperature for another 30 minutes. Then, a drop of n-butylamine was added, and the resultant solution was heated for 22 hours at 40° C. Further, a drop of n-butylamine was added, and the resultant solution was heated for 31 hours at the same temperature. After the reaction solution was cooled to room temperature, methanol was added to the reaction solution. Then, the solvent was removed by a rotary evaporator. By purifying the residue by silica gel column chromatography (eluant: ethyl acetate:n-hexane=2:1), 12 mg of 1,7-bis(4'-hydroxy-3'-trifluoromethoxyphenyl)-4-acetoxypropyl-1,6-heptadiene-3,5-dione having a melting point of 130 to 131° C. was obtained.

$^1$HNMR (CDCl$_3$): δ1.86 to 1.93 (m, 2H), δ2.09 (s, 3H), δ2.63 to 2.67 (m, 2H), δ4.18 (t, J=6.2 Hz, 2H), δ5.62 (s, 2H), δ6.95 (d, J=15.6 Hz, 2H), δ7.08 (d, J=8.0 Hz, 2H), δ7.43 to 7.47 (arom.H, 4H), δ7.68 (d, J=15.6 Hz, 2H).

Synthetic Example 4

Synthesis of 1,7-bis(4'-acetoxy-3'-trifluoromethoxyphenyl)-4-methoxycarbonylethyl-1,6-heptadiene-3,5-dione (compound 17)

Triethylamine 270 mg was added under room temperature to a THF 10 mL solution containing 1,7-bis(4'-hydroxy-3'-trifluoromethoxyphenyl)-4-methoxycarbonylethyl 1,6-heptadiene 3,5-dione 500 mg and acetic anhydride 272 mg, and the resultant solution was agitated for 2 hours at room temperature. After the reaction was ended, water was poured, and the resultant solution was subjected to extraction with ethyl acetate. The extract was dried with sodium sulfate, and the solvent was removed. The crystal residue was washed with a small quantity of ethanol, filtered, and dried, whereby 430 mg of 1,7-bis(4'-acetoxy-3'-trifluoromethoxyphenyl)-4-methoxycarbonylethyl-1,6-heptadiene-3,5-dione having a melting point of 149 to 150° C. was obtained.

$^1$HNMR (CDCl$_3$): δ2.36 (s, 6H), δ2.53 to 2.57 (m, 2H), δ2.93 to 2.97 (m, 2H), δ3.69 (s, 3H), δ7.09 (d, J=15.2 Hz, 2H), δ7.26 (d, J=8.4 Hz, 2H), δ7.53 to 7.56 (arom.H, 4H), δ7.72 (d, J=14.8 Hz, 2H).

Synthetic Example 5

Synthesis of 1,7-bis(4'-hydroxy-3'-trifluoromethoxyphenyl)-4-[2'-(tetrahydropyran-4-yl)oxyethoxyethyl]-1,6-heptadiene-3,5-dione An ethyl acetate (2 mL) solution containing 3-[2'-(tetrahydropyran-4-yl)oxyethoxyethyl]-pentane-2,4-dione 245 mg (0.90 mmol) and diboron trioxide 51 mg (0.72 mmol) was heated for 30 minutes to 40° C., and then 4-hydroxy-3-(trifluoromethoxy)benzaldehyde 370 mg (1.8 mmol) and tri-n-butyl borate 0.49 mL (1.8 mmol) were added. The resultant solution was continued to be heated for another 30 minutes at the same temperature. Then, an ethyl acetate (0.2 mL) solution containing n-butylamine 0.09 mL (0.9 mmol) was added, and the resultant solution was heated for 3 hours at the same temperature. After the reaction solution was cooled to room temperature, 1M-hydrochloric acid (3 mL) was added, and the resultant solution was vigorously agitated for 10 minutes. Ethyl acetate 20 mL was added to the reaction solution. The organic layer was washed with 0.5M-hydrochloric acid, further washed with a saturated sodium bicarbonate water solution and with a saturated saline solution, and then dried with magnesium sulfate. The solvent was removed by a rotary evaporator. The residue was purified by a silica gel column chromatography (eluant: ethyl acetate:n-hexane=1:2). Then, 290 mg of 1,7-bis(4'-hydroxy-3'-trifluoromethoxyphenyl)-4-[2'-(tetrahydropyran-4-yl)oxyethoxyethyl]-1,6-heptadiene-3,5-dione was obtained as an oily matter.

$^1$HNMR (CDCl$_3$): δ1.4 to 1.8 (6H), δ2.30 (about 0.9H, q, J=7 Hz), δ2.86 (about 1.3H, t, J=7 Hz), δ3.4 to 3.7 (8H), δ4.43 (about 0.8H, t, J=7 Hz), δ4.57 (1H, m), 5.78 (1H, br.s), δ5.89 (1H, br.s), δ6.6 to 7.1 (4H), δ7.4 to 7.7 (6H), δ17.64 (about 0.6H, s)

$^{19}$FNMR (CDCl$_3$): δ-59.45 (s), δ-59.40 (s)

Synthetic Example 6

Synthesis of 1,7-bis(4'-hydroxy-3'-trifluoromethoxyphenyl)-4-(2'-hydroxyethoxyethyl)-1,6-heptadiene-3,5-dione (compound 22)

A quantity of 53 mg (0.08 mmol) of 1,7-bis(4'-hydroxy-3'-trifluoromethoxyphenyl)-4-[2'-(tetrahydropyran-4-yl)oxyethoxyethyl]-1,6-heptadiene-3,5-dione obtained in synthetic example 5 was dissolved in 2 mL of ethanol. Concentrated hydrochloric acid (0.02 mL) was added to this solution and the resultant solution was agitated for 2 hours at room temperature. The solution obtained by adding ethyl acetate (30 mL) was washed with water, further washed with a saturated sodium bicarbonate aqueous solution and with a saturated saline solution, and then dried with magnesium sulfate. A small quantity of dichloromethane was added to the residue obtained by removing the solvent by a rotary evaporator, and the resultant mixture was left to stand at room temperature. Then, 35 mg of 1,7-bis(4'-hydroxy-3'-trifluoromethoxyphenyl)-4-(2'-hydroxyethoxyethyl)-1,6-heptadiene-3,5-dione having a melting point of 112 to 114° C. was obtained.

$^1$HNMR ($d_6$DMSO): δ2.07 (about 1H, m), δ2.93 (about 1H, m), δ3.3 to 3.5 (6H), δ4.70 (about 0.5H, t, J=7 Hz), δ6.9 to 7.3 (4H), δ7.5 to 7.8 (6H), δ10.81 (1H, br.s), δ10.88 (1H, br.s), δ17.95 (about 0.5H, s)

$^{19}$FNMR ($d_6$DMSO): δ-58.38 (s), δ-58.24 (s)

Test Example 1

Senile Plaque Binding Test

A quantity of 2 mg of each of compounds (1), (2), (4), (15), and (23) was measured, and dimethyl sulfoxide (DMSO) 1 ml was added to each of the measured compounds to dissolve the compound. Then, 200 µl of each of the mixture was measured, and a 0.3%-Triton X100-containing 100 mM-phosphate buffer (pH 7.4) (hereinafter, PBS-T) was added thereto to make a 4 ml test solution (concentration of the chemical solution: 100 µg/ml).

First, in order to prevent nonspecific adsorption of protein, a fixed sample of human brain tissue of an Alzheimer's disease case (20 µm thick) was immersed in PEST 4 ml containing 2% bovine serum albumin (BSA), and the mixture was left at room temperature for 1 hour to react. Then, the mixture was caused to react with a rabbit antihuman amyloid β polyclonal antibody (IBL, 0.2 µg/ml) overnight at 4° C.

Further, the sample was washed with PBS-T for 10 minutes 3 times, and then was caused to react with Alexa 647 anti-rabbit IgG antibody (Molecular Probes, 500-fold dilution) for 4 hours at room temperature. The sample was washed with PBS-T for 10 minutes 3 times, and then immersed in each 4 ml test solution containing a corresponding compound, and left to stand in the test solution at room temperature with the light shielded. After 1 hour, the sample was taken out, and washed with PBS-T for 5 minutes 3 times, and then washed with PBS-T for 10 minutes 3 times. Then, the sample was further washed with distilled water, and enclosed with glycerol, and this sample was used for observation. The binding capacity of each compound to the amyloid β protein was observed by an inverted fluorescence microscope (IX70, Olympus). It should be noted that a compound image was measured by means of an FITC filter (excitation wavelength: 450 to 480 nm, detection filter: long path filter of 515 nm or more), and an amyloid β protein image was measured by means of a Cy5 filter (excitation wavelength: 630 to 650 nm, detection filter: 671 to 693 nm). As a negative control test, the same staining treatment was performed by use of a 0.1%-DMSO-containing PBS-T solution.

Figure 2:
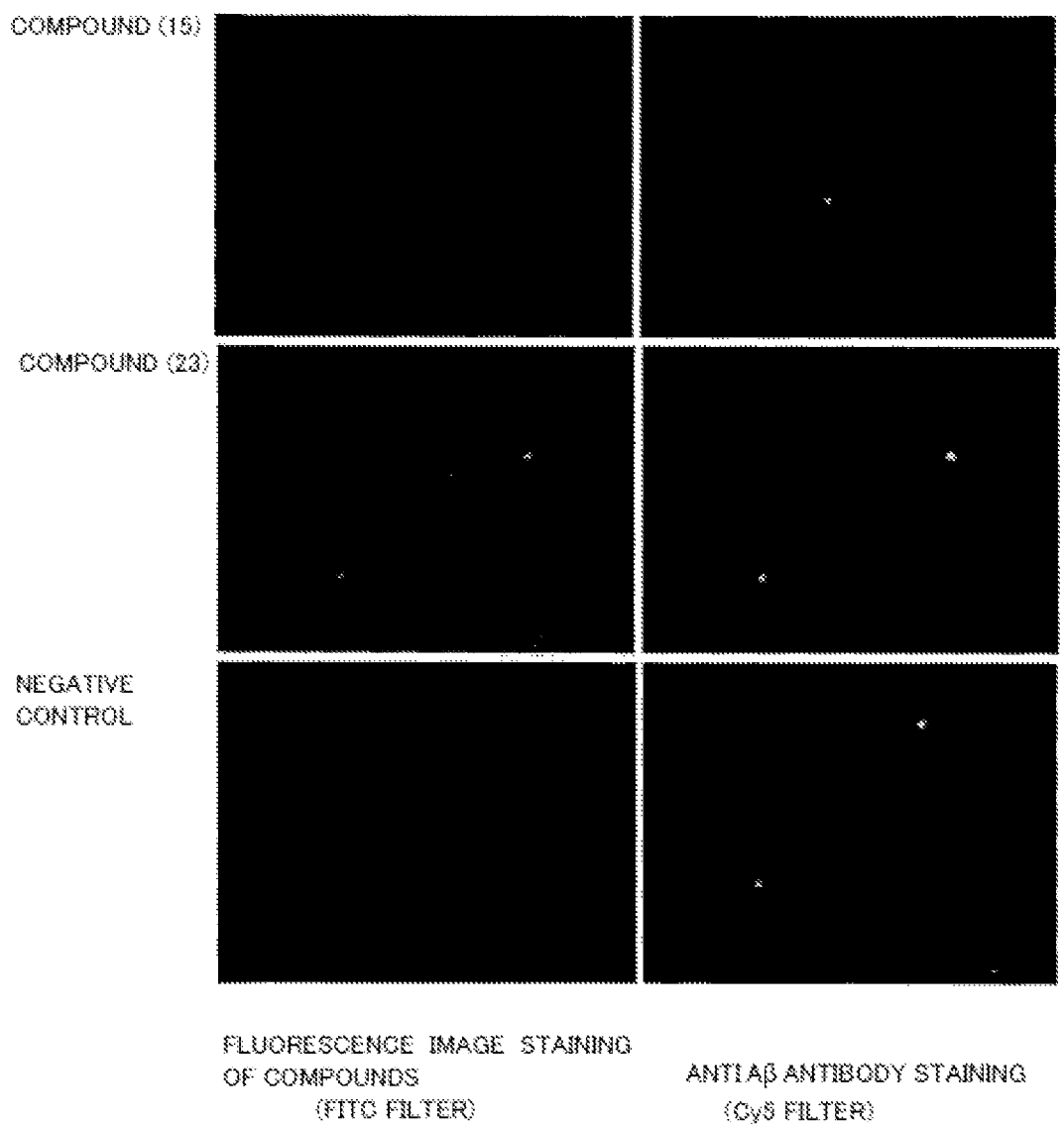
FIG. 2 shows stain images of slices of a cortex of a temporal lobe of a postmortem brain of an Alzheimer's disease patient.

FIG. 1 and FIG. 2 show fluorescent stain images of the compound of the present invention and stain images of senile plaques by an anti-amyloid β antibody, in slices of the cortex of the temporal lobe of a postmortem brain of an Alzheimer's disease patient. The left column shows the fluorescent stain images of the compounds (FITC filter), and the right column shows the stain images of the amyloid β antibody (Cy5 filter). The compounds of the present invention had affinities to the amyloid β proteins forming senile plaques, and fluorescent stain images of the compounds were observed at the same positions of the senile plaques. In the negative control, fluorescent stain images specific to senile plaques were not observed.

Other compounds shown in table 1 also show high affinities to the amyloid β protein.

Test Example 2

$^{19}$F-MR Image Measurement

A quantity of 4.5 mg of compound (I) was measured, and 0.112 ml of Cremophol EL was added to the measured compound. The compound was dissolved by use of a glass stick while the mixture being heated. Then, 0.45 ml of saline was added to the mixture to prepare an administration solution (8 mg/ml).

This administration solution 250 µl was administered, in one shot (about 90 seconds), to the tail vein of an amyloid precursor protein transgenic mouse (Tg2576, created according to the method disclosed in Science, 274,99 (1996)) under anesthesia by pentobarbital sodium.

After the administration was ended, with the mouse under anesthesia, the head of the mouse was continuously measured in units of 1 hour by use of an MRI device. Then, pieces of data were added to create images. $^{19}$F-MRI brain images were obtained by chemical shift imaging method (CSI method). The MRI device that was used was 7T Unity Inova MR Scanner (by Varian).

Figure 3:
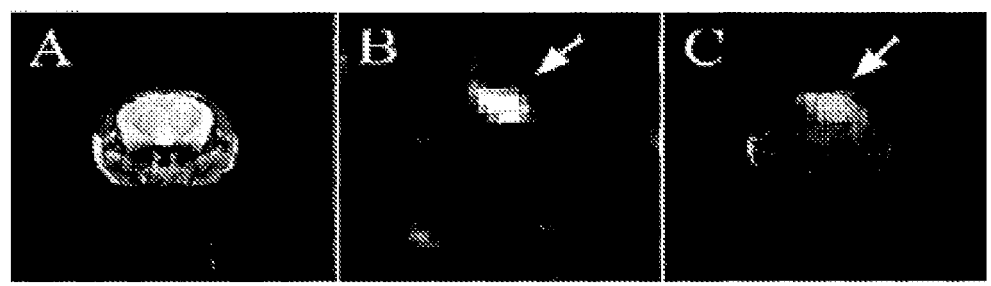
FIG. 3 shows in vivo $^1$H-MRI and $^{19}$F-MRI brain images when compound (I) is administered to an amyloid precursor protein transgenic mouse.

FIG. 3 shows MRI brain images which were obtained by measuring for 3 hours after 3 hours had elapsed after the administration. In FIG. 3, A shows a $^1$H-MRI image, B shows a $^{19}$F-MRI image, and C shows a merged image of A and B. In the $^{19}$F-MR image, signals that are assumed to be corresponding to a senile plaque were detected in the brain (arrow).

Test Example 3

Brain Tissue Staining

The brain of the mouse scanned by $^{19}$F-MRI in test example 2 was taken out and fixed for 2 days in a 4%-formalin solution, and then placed in a 15%-sucrose solution for cryoprotection. Then, a 20 µm-thick slice was created by a cryostat. Next, the slice was caused to react with a rabbit anti-human amyloid β polyclonal antibody (IBL, 0.2 µg/ml) at 4° C. overnight. Further, the sample was washed with PBS-T for 10 minutes 3 times, and then caused to react with Alexa 647 anti-rabbit IgG antibody (Molecular Probes, 500-fold dilution) for 4 hours at room temperature. This sample was washed with PBS-T for 10 minutes 3 times, and then counterstained with cresyl violet for 1 minute. Then, the sample was further washed with distilled water, and then enclosed with glycerol, and this sample was used for observation. The binding capacity of the compound to a senile plaque was observed by an inverted fluorescence microscope. It should be noted that a compound image was measured by use of the FITC filter and an amyloid β protein image was measured by means of the Cy5 filter. The same treatment was performed onto a normal mouse.

Figure 4:
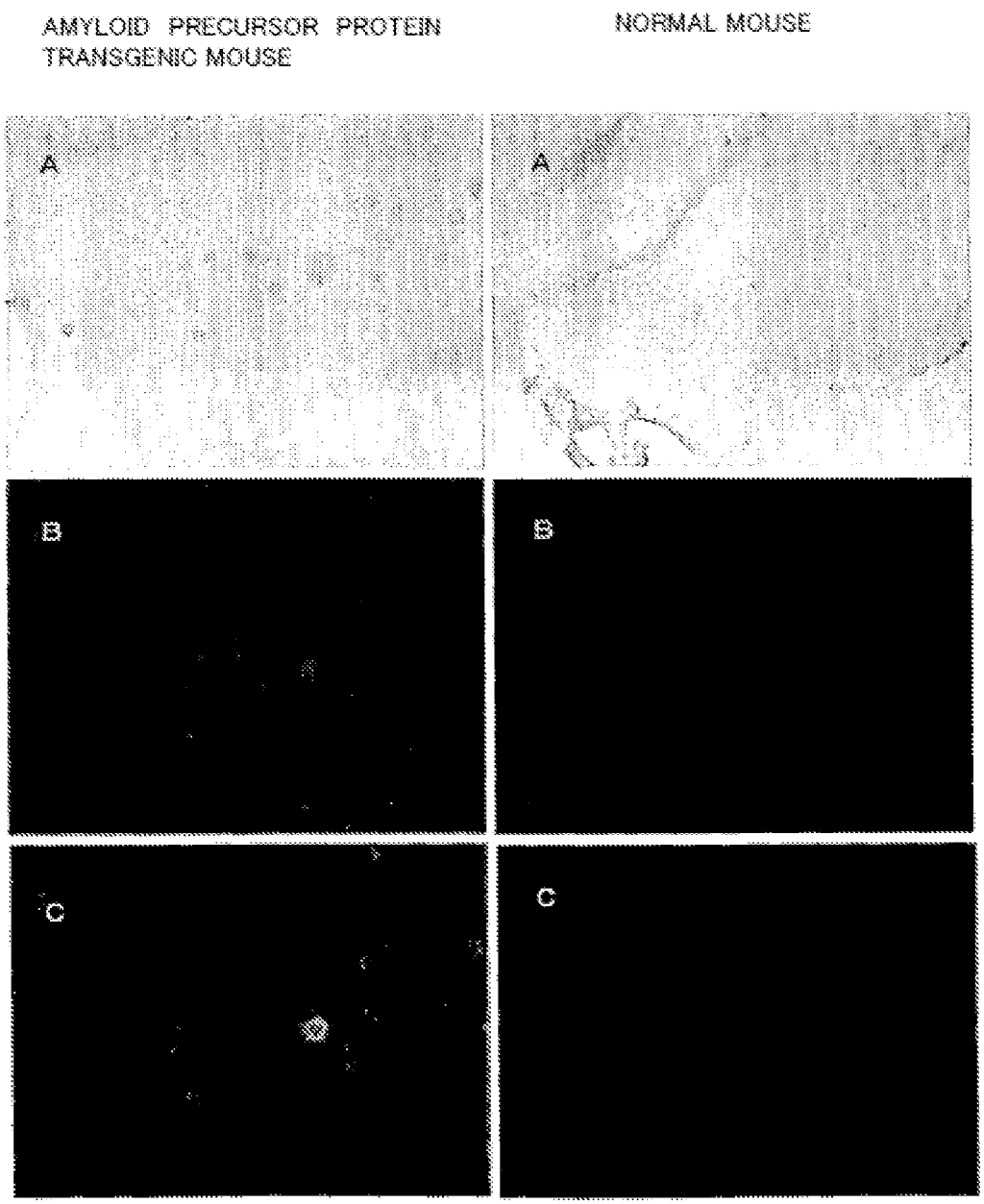
FIG. 4 shows stain images of mouse brain slices when compound (I) is administered to an amyloid precursor protein transgenic mouse and a normal mouse.

FIG. 4 shows obtained stain images of the slices of the brains of the mice. In FIG. 4, the left column shows amyloid precursor protein transgenic mouse images, and the right column shows normal mouse images. A shows bright-field images (cresyl violet counterstain), B shows fluorescent stain images of compound (I), and C shows β amyloid antibody stain images. The spots of amyloid β forming senile plaques observed in C coincide with fluorescent stain images of compound (I) observed in B. Thus, the transmissiveness of the compound of the present invention through the blood-brain barrier and sufficient binding of the compound of the present invention to senile plaques in vivo were confirmed.

Test Example 4

NMR Measurement of Presence Proportion of Keto Form and Enol Form in Solution

With respect to a compound that exists mainly as the keto form in water and exists mainly as the enol form in a low polarity organic solvent, whether such a compound tends to exist as the enol form or as the keto form was confirmed, by selecting as a solvent a highly polar deuterium substitution-containing dimethyl sulfoxide ($d_6$DMSO), and by comparing the area intensities of two peaks (resulting from the keto form and the enol form) by $^{19}$FNMR. In order to determine the correspondence between the two signals and the keto and enol forms, it is necessary to calculate in advance a rough keto form/enol form ratio by $^1$HNMR. That is, in $^1$HNMR, the presence of the triplet appearing around δ4.5 ppm (resulting from the keto form) and the singlet appearing around δ17.8 ppm (resulting from the enol form) is confirmed, and a rough keto form/enol form ratio is obtained from the area intensities (the obtained area intensity ratio does not precisely reflect the keto form/enol form ratio due to a large chemical shift distance). Then, $^{19}$FNMR was measured, and from the area intensity ratio of the peak of the fluorine that should be resultant from the keto form and the peak of the fluorine that should be resultant from the enol form, a precise keto form/enol form ratio was determined (a precise area intensity ratio can be determined as a result of a small chemical shift distance).

Figure 5:
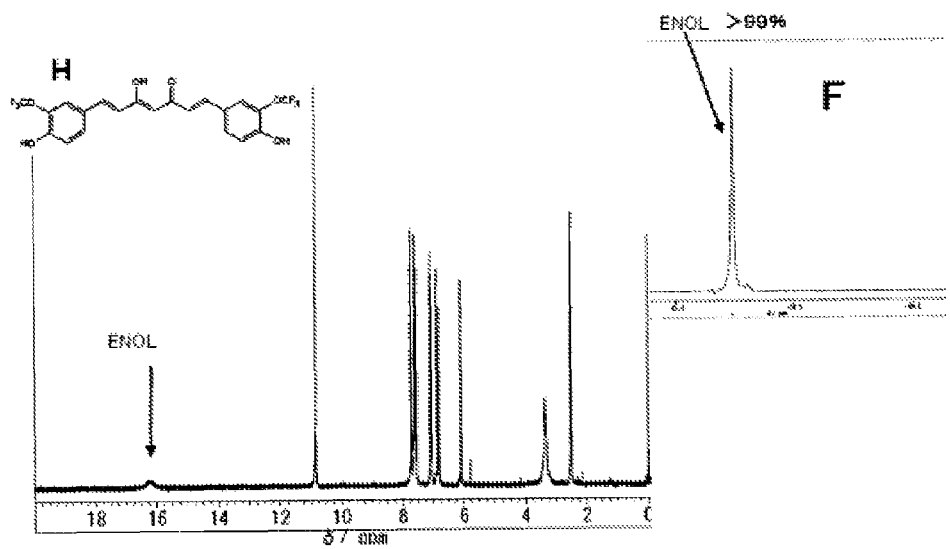
FIG. 5 shows a result of an NMR measurement of compound 23.
Figure 6:
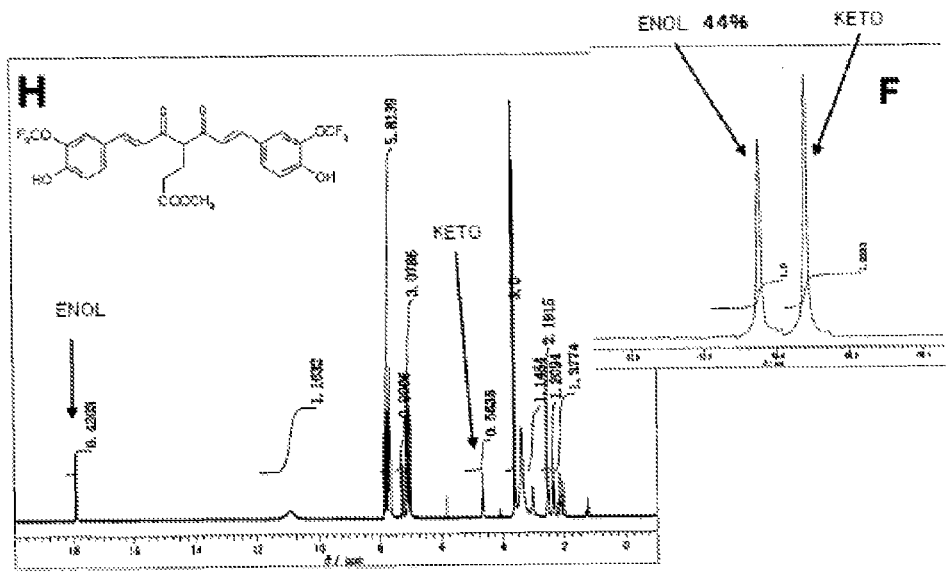
FIG. 6 shows a result of an NMR measurement of compound 1.
Figure 7:
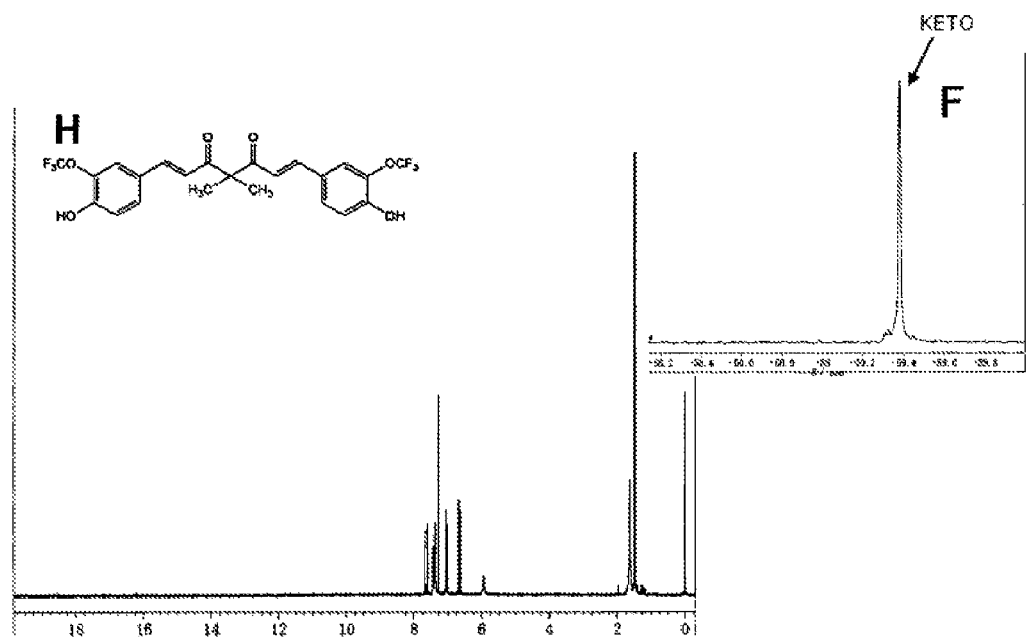
FIG. 7 shows a result of an NMR measurement of compound 24.
Figure 8:
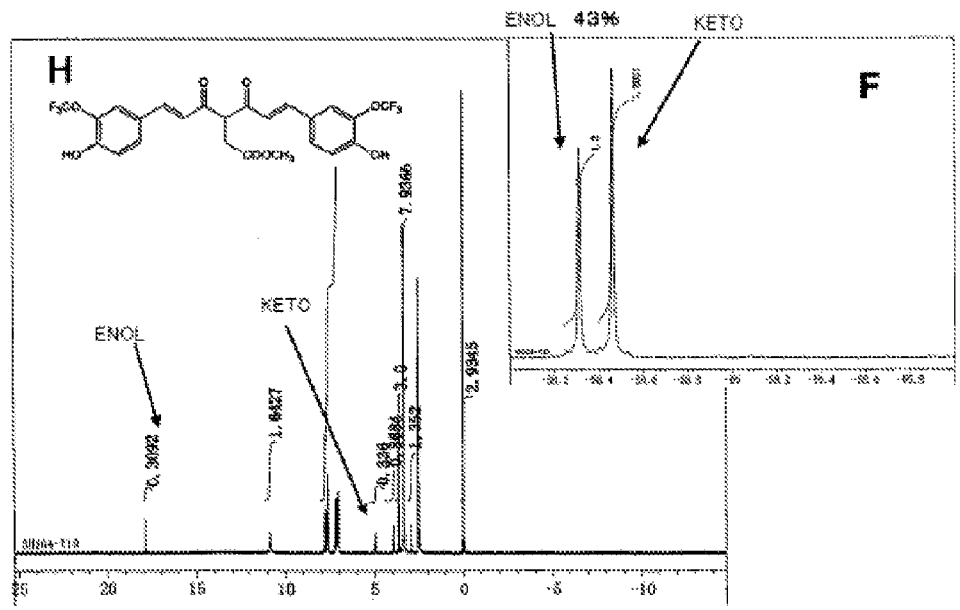
FIG. 8 shows a result of an NMR measurement of compound 5.
Figure 9:
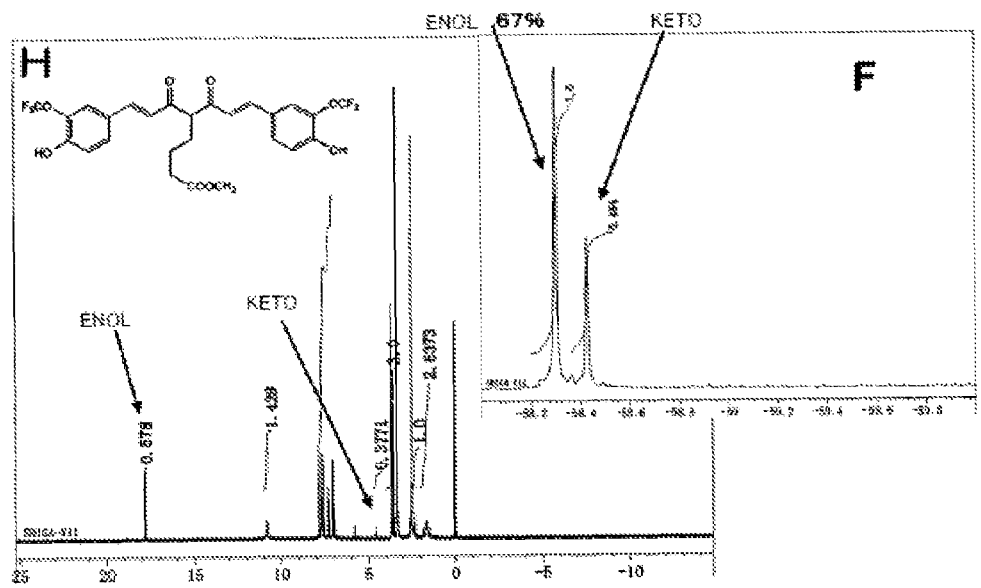
FIG. 9 shows a result of an NMR measurement of compound 6.
Figure 10:
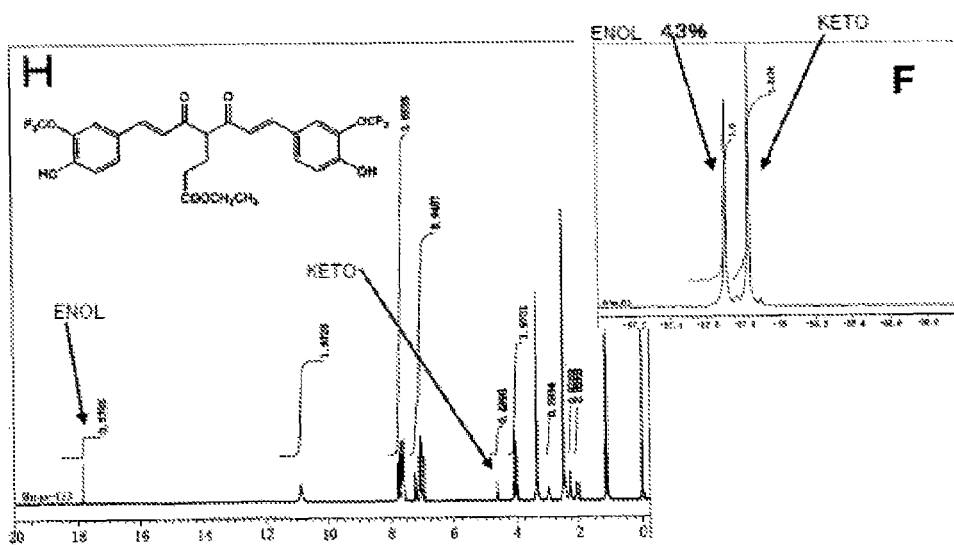
FIG. 10 shows a result of an NMR measurement of compound 8.
Figure 11:
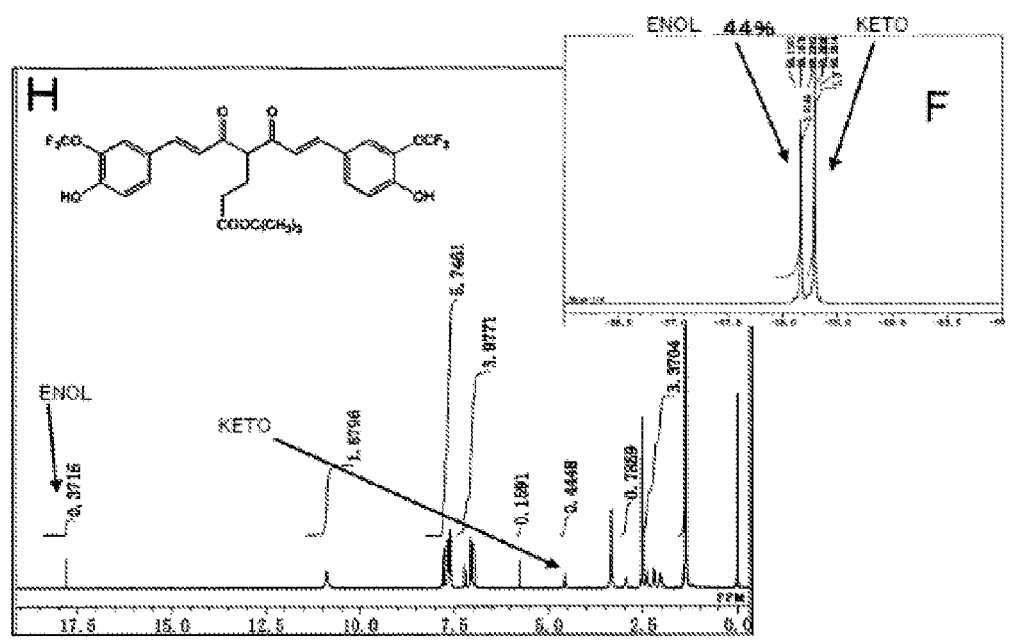
FIG. 11 shows a result of an NMR measurement of compound 9.

Now, representative examples will be shown. FIG. 5 shows an NMR measurement result of compound 23, FIG. 6 shows an NMR measurement result of compound 1, FIG. 7 shows an NMR measurement result of compound 24, FIG. 8 shows an NMR measurement result of compound 5, FIG. 9 shows an NMR measurement result of compound 6, FIG. 10 shows an NMR measurement result of compound 8, and FIG. 11 shows an NMR measurement result of compound 9. With respect to the keto form and the enol form, NMR signals of fluorine are detected at different chemical shift positions, respectively, by the NMR measurement. Accordingly, the presence proportion of the keto form and the enol form can be calculated. This is applied to other compounds, of the present invention, that have fluorine atoms.

Test Example 5

Figure 12:
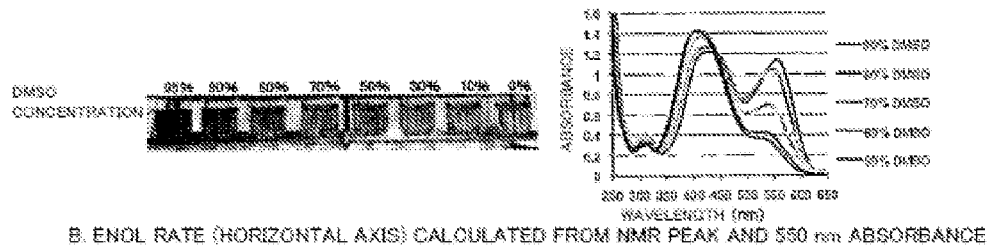
FIG. 12 A shows colors and chromatic spectra of DMSO solutions of various concentrations containing compound 1 dissolved at a concentration of 20 µg/ml, and B shows the relationship between the enol rate calculated from NMR peaks and the 550 nm absorbance.
Figure 12:
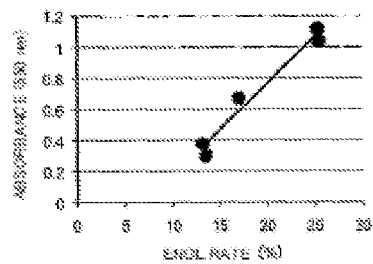

Measurement of Presence Proportion of the Keto Form and the Enol Form in Solution and Color Measurement of Solution Compound 1 was dissolved into DMSO solutions each having a concentration of 95%, 90%, 80%, 70%, 50%, 30%, 10%, 0%, such that the concentration of compound 1 was 20 μg/ml, and chromatic spectrum was measured and NMR measurement was performed for each solution. As a result, as shown in FIG. 12A, the color varied depending on the DMSO concentration. In chromatic spectra, the absorbance at a wavelength of 550 nm which corresponds to red varied. Next, each solution was subjected to NMR measurement, and from the area ratio of the fluorine peaks, the presence proportion of the keto form and the enol form was calculated. As a result, as shown in FIG. 12B, as the proportion of the enol form increased, red becomes stronger, and absorbance at 550 nm increases. Thus, both are highly correlated with each other.

Test Example 6

Binding Property Test of Synthesized Compound to Amyloid β Peptide Aggregate

The binding capacity of the compounds to an amyloid β peptide aggregate was quantitatively measured by a thioflavin-T fluorescence inhibition test.

First, amyloid β peptides (1-40, Peptide Institute, Minohshi, Osaka) were dissolved in a 50 mM phosphate buffer containing 100 mM sodium chloride (pH 7.5) such that the concentration of the amyloid β peptides was 100 mM, and then the solution was left to stand for 16 hours at 30° C., thereby producing amyloid β peptide aggregates. To these amyloid β peptide, amyloid β peptide aggregates that had been prepared in advance by the same method and sonicated for 30 minutes under 28-45-100 KHz variation were added by a 1/1000 quantity, whereby uniform amyloid β peptide aggregates were prepared.

The amyloid β peptide aggregates prepared by the above method, thioflavin-T, and a measurement compound were added in a 50 mM phosphate buffer (pH 7.4) such that the final concentrations thereof were 1 μM, 3 μM, and 0.02 to 20 μM, respectively. The resultant solution was cause to react for 30 minutes at 23° C. with the light shielded. Then, the fluorescence of thioflavin-T was measured under a condition of Ex=440 nm, Em=490 nm, Cutoff filter=475 nm. The $IC_{50}$ values were calculated by using an analysis software, GraphPad PRISM Ver.5 (GraphPad Software, Inc.).

As a result, the values of representative compounds are shown in the table below. For comparison, measurement was performed also on compound 23 which was rich in the enol form structures and compound 24 which existed in 100% keto form structures. As a result, the $IC_{50}$ value of compound 23 which was rich in the enol form structures was 0.21 μM, and compound 23 strongly bound to amyloid β peptide aggregates. The $IC_{50}$ value of compound 24 which existed in 100% keto form structures was >15 μM. Thus, it was confirmed that compound 24 scarcely bound to amyloid β peptide aggregates.

TABLE 4

| | Structural formula | Amyloid binding property ($IC_{50}$) | Physical property |
|---|---|---|---|
| Compound 23 | $F_3CO$—⟨aryl(OH)⟩—CH=CH—C(=O)—CH_2—C(=O)—CH=CH—⟨aryl(OH)⟩—$OCF_3$ | 0.21 μM | m.p. 172-173° C. |
| Compound 1 | $F_3CO$—⟨aryl(OH)⟩—CH=CH—C(=O)—CH(CH_2CH_2COOCH_3)—C(=O)—CH=CH—⟨aryl(OH)⟩—$OCF_3$ | 0.44 μM | |

TABLE 4-continued

| Structural formula | Amyloid binding property (IC$_{50}$) | Physical property |
|---|---|---|
| Compound 24 | >15 μM | Oily matter |
| Compound 5 | 0.52 μM | |
| Compound 6 | 0.31 μM | |
| Compound 8 | 0.38 μM | |
| Compound 9 | 0.65 μM | |
| Compound 2 | 1.3 μM | |

TABLE 5

Table continued

| | | |
|---|---|---|
| Compound 7 | 0.14 μM | |

TABLE 5-continued

| Compound 19 | (structure: bis(4-sodiumoxy-3-trifluoromethoxyphenyl) curcuminoid with COOCH₃ side chain) | 0.56 μM | |
| Compound 20 | (structure: bis(4-hydroxy-3-trifluoromethoxyphenyl) curcuminoid with OCH₂OCH₃ side chain) | 0.50 μM | |
| Compound 21 | (structure: bis(4-hydroxy-3-trifluoromethoxyphenyl) curcuminoid with CON(CH₃)₂ side chain) | 0.50 μM | |
| Compound 22 | (structure: bis(4-hydroxy-3-trifluoromethoxyphenyl) curcuminoid with OCH₂CH₂OH side chain) | 0.70 μM | |
| Compound 25 | (structure: curcumin mono-O-CH₂COOCH₃ derivative) | 0.14 μM | mp. 88-90° C. |
| Compound 26 | (structure: curcumin mono-O-CH₂COOH derivative) | 0.31 μM | mp. 190-192° C. (dec) |
| Compound 27 | (structure: asymmetric curcuminoid with one 3-CF₃-4-OH phenyl and one 3-OCH₃-4-OH phenyl) | 0.13 μM | mp. 200° C. |
| Compound 28 | (structure: bis(4-methylamino-3-trifluoromethylphenyl) curcuminoid) | 5.8 μM (hardly soluble) | mp. 192-194° C. |

TABLE 5-continued

Table continued

| | | |
|---|---|---|
| Compound 29 | 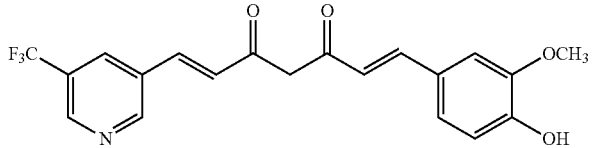 [SMILES: COc1cc(/C=C/C(=O)CC(=O)/C=C/c2cncc(C(F)(F)F)c2)ccc1O] | 0.10 μM mp. 187-189° C. |
| Compound 14 | 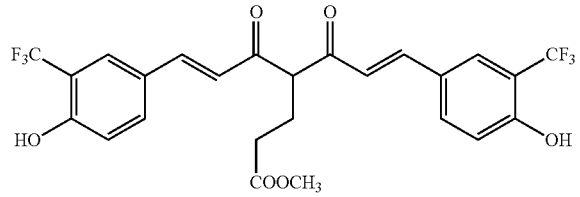 [SMILES: COC(=O)CCC(C(=O)/C=C/c1ccc(O)c(C(F)(F)F)c1)C(=O)/C=C/c1ccc(O)c(C(F)(F)F)c1] | 0.36 μM |
| Compound 15 | 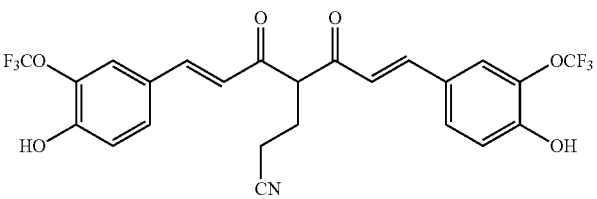 [SMILES: N#CCCC(C(=O)/C=C/c1ccc(O)c(OC(F)(F)F)c1)C(=O)/C=C/c1ccc(O)c(OC(F)(F)F)c1] | 0.30 μM |

TABLE 6

Table continued

| | | |
|---|---|---|
| Compound 16 | 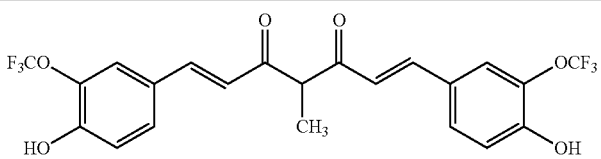 [SMILES: CC(C(=O)/C=C/c1ccc(O)c(OC(F)(F)F)c1)C(=O)/C=C/c1ccc(O)c(OC(F)(F)F)c1] | 0.32 μM |
| Compound 30 | 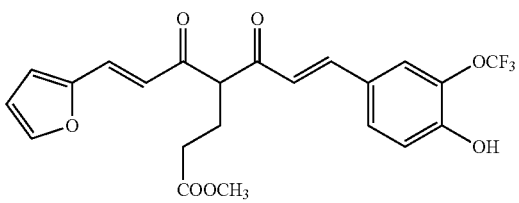 [SMILES: COC(=O)CCC(C(=O)/C=C/c1ccc(O)c(OC(F)(F)F)c1)C(=O)/C=C/c1ccco1] | 0.65 μM mp. 141° C. |

In the above tables, the compounds of the present invention are indicated in the keto form. However, the compounds other than compound 24 can take the enol form through the keto-enol tautomerism.

Test Example 7

Figure 13:
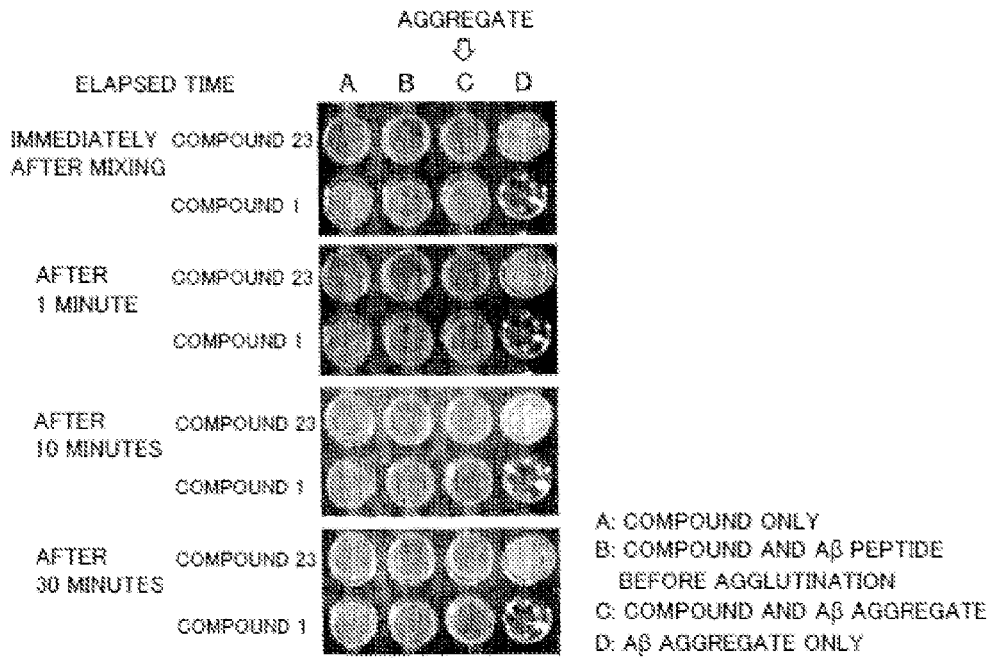
FIG. 13 shows, with respect to each of compound 23 and compound 1, results of observations of colors, over time from the start of the reaction, of a solution containing only the corresponding compound, a solution containing the corresponding compound and amyloid β peptide aggregates, a solution containing the corresponding compound and amyloid β peptides before agglutination reaction, and a solution containing amyloid aggregates only.

Model Experiment of In-Vitro Diagnostic Agent for Alzheimer's Disease Utilizing Keto-Enol Tautomerism Amyloid β peptide aggregates were prepared by the method described in test example 6, and caused to precipitate in the solution by prolonging the reaction time. After the aggregates were prepared in this manner, the precipitation containing the amyloid β peptide aggregates and a supernatant not containing the amyloid β peptide aggregates were separated. The precipitation containing the amyloid aggregates was suspended at a concentration of 100 μM, in a buffer. Then, each of compounds 23 and 1 was dissolved at a concentration of 20 μg/ml in a 50 mM phosphate buffer (pH 7.5) containing 100 mM NaCl. For each compound, four kinds of liquid mixtures were prepared, that is, a liquid mixture obtained by adding 100 μl of a buffer into 100 μl of the compound containing solution (A of FIG. 13); a liquid mixture obtained by adding 100 μl of a buffer in which amyloid β peptides before agglutination reaction were dissolved, to 100 μl of the compound containing solution (B of FIG. 13); a liquid mixture obtained by adding 100 μl of a buffer in which amyloid β peptide aggregates were suspended, to 100 μl of the compound containing solution (C of FIG. 13); and a liquid mixture obtained by adding 100 μl of a buffer in which amyloid β peptide aggregates were suspended, to 100 μl of a buffer not containing a compound (D of FIG. 13). Then, the four kinds of liquid mixtures were left to stand at room temperature. FIG. 13 shows the result. Only the sample in which compound 1 and amyloid β peptide aggregates were mixed began to be stained in red after 5 minutes, and the color became gradually stronger and changed into strong red after about 30 minutes. The color of the sample in which the amyloid β peptides before agglutination reaction were added did not change. When the absorption spectrum of the sample that had turned into red was measured, the peak had shifted towards a longer wavelength. Since red is observed in the enol form, this result shows that the enol form of compound 1 bound to the amyloid β peptide aggregates. As a result, it is considered that the keto/enol equilibrium in the solution was lost, and structural changes happened, that is, the keto bodies newly turned into enol bodies in the solution. Further, the solution color of the sample in which amyloid β peptides before agglutination reaction had been added did not change. This shows that, with respect to compound 1, when amyloid β peptide aggregates exist, the enol form having a high aggregate binding capacity increases in number, whereby the color turns into red. This shows that compound 1 serves as a reagent that indicates the presence of amyloid β peptide aggregates in the solution.

Test Example 8

Figure 14:
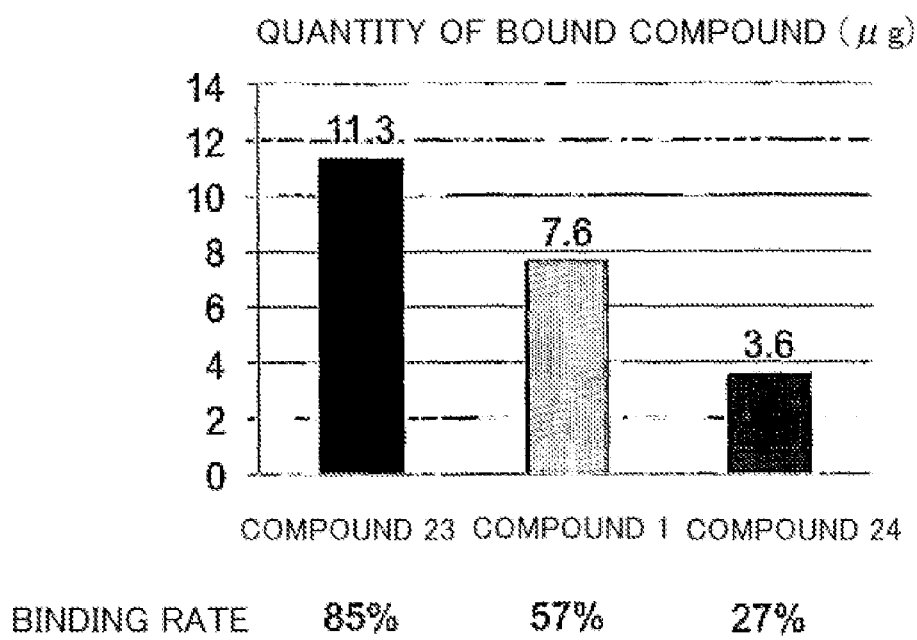
FIG. 14 shows the quantity of bound compound and the binding rate, of each of compound 23, compound 1, and compound 24, to amyloid β peptide aggregates.

The Compound that Bound to an Amyloid β Peptide Aggregate in the Enol Form is Released from the Amyloid β Peptide Aggregate when the Compound Transforms into the Keto Form Each of compound 23, compound 1, and compound 24 is dissolved at a concentration of 2 μg/mL, in a phosphate buffer, and then amyloid β peptide aggregates are added to each solution, and the resultant solution is caused to react for 1 hour. Then, the solution is centrifuged for 10 minutes at 6,000 rpm, to separate the amyloid β peptide aggregates. A supernatant was removed, and an absorbance measurement was performed to measure the quantity of the compound that had not bound to the amyloid peptide aggregates and that were contained in the supernatant. The obtained quantity was subtracted from the original quantity of the compound, whereby the quantity of the compound that had bound to the amyloid β peptide aggregates was calculated. FIG. 14 shows the result. With respect to the binding rate, compound 23, which was rich in the enol form, showed the highest binding rate, 85%, compound 24, which was composed of the keto form only, showed the lowest binding rate, 27%, and compound 1, whose characteristic is between those of compound 23 and compound 24, showed 57%. From the result above, it is found that compound 24, which is composed of the keto form only, has a weak binding property to amyloid β peptide aggregates.

Figure 15:
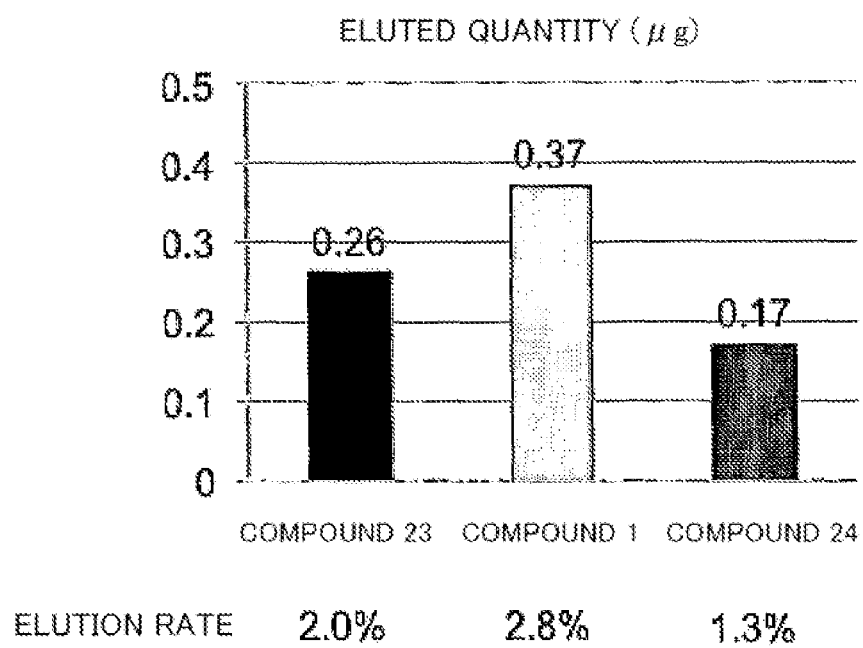
FIG. 15 shows the quantity, of each of compound 23, compound 1, and compound 24, that is released when precipitated amyloid β peptide aggregates are washed and then a buffer is added, and the rate of the quantity in its original quantity (100%).

Next, the precipitated amyloid β peptide aggregates were washed, a buffer was added thereto, and the quantity of the compound that got released was measured. Then, the rate of the compound that had bound to amyloid β peptide aggregates and then was eluted into the buffer was calculated using the original quantity of the compound as 100%. FIG. 15 shows the result. As a result, compound 1 which transforms into the keto form more readily than compound 23 showed the highest value. It is suggested that the compound that readily transforms into the keto form is promptly excreted after the binding.

Further, with respect to an NMR, when the compound signal strongly binds to an amyloid β peptide aggregate, its free movement is reduced, theoretically resulting in a broad NMR signal. Due to the keto-enol tautomerism, a compound that has a tautomerism that allows the compound to be repeatedly bound to and released from a senile plaque at a local site where senile plaques exist will emit a stronger NMR signal.

Test Example 9

Quantity Determination of Amyloid β Peptide Aggregates Using Keto-Enol Tautomerism Preparation of Anti-Amyloid β (Aβ) Antibody Binding Microspheres A quantity of 25 μL of Protein G microspheres (by Polysciences, Inc., No. 21106-1) was measured and placed into a 1.5 mL microtube, and was washed with PBS-T 3 times. The washing operation was performed as follows: 0.75 mL of PBS-T was added, the resultant mixture was centrifuged at 10,000×G for 5 minutes, and then the supernatant was removed. A quantity of 0.05 mL of an anti-amyloid β monoclonal antibody (in-house hybridoma clone 1A-10F producing antibody, mouse IgG1, 1 mg/mL) and 0.05 ml of PBS-T were added to the washed microspheres, and the resultant mixture was caused to react for 1 hour at 4° C. During the reaction, the mixture was agitated every 5 to 15 minutes. After the reaction, the microspheres were washed 3 times by the same method above, then suspended in PBS-T 0.25 mL, and kept at 4° C. until they were used.

Negative control microspheres were prepared by use of a nonspecific mouse IgG1 antibody (by SIGMA, No. M 9269, mouse myeloma-derived IgG1, 1 mg/mL) by the same method.

Quantity Determination 1 of Amyloid β Aggregates

Figure 16:
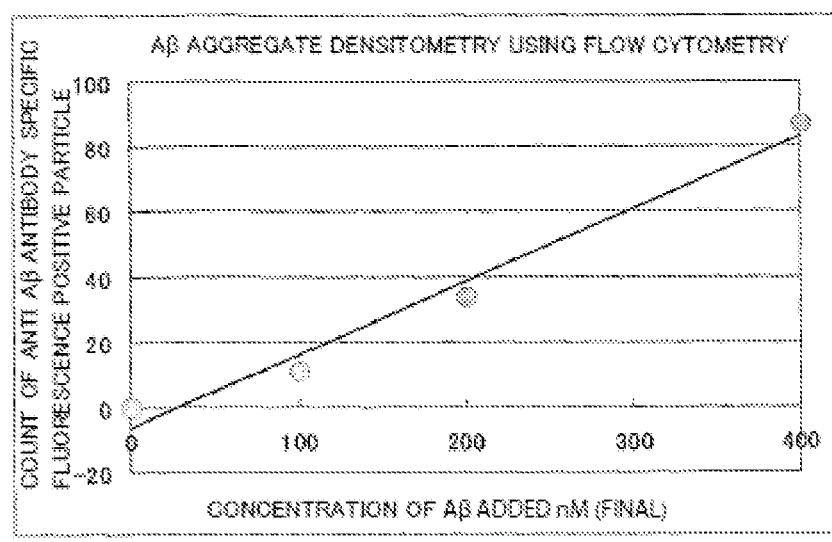
FIG. 16 shows a result of densitometry of amyloid β peptide aggregates by use of flow cytometry.

The above prepared anti-amyloid β antibody binding microspheres, the invention compound 1, and amyloid β peptide aggregates prepared by the same method as in test example 6 were mixed, and the mixture was caused to react for 5 to 60 minutes at 4° C. Then, by a method using a flow cytometer (FACS) (by Becton Deckinson, FACS Calibur), fluorescence intensity analysis was performed with respect to the invention compound 1 that had bound to the microspheres via the specific antibody and the amyloid β aggregates. By subtracting as a background the analysis value of the negative control microspheres to which the nonspecific mouse IgG1 antibody was bound, the number of counts of anti Aβ antibody-specific fluorescence positive microsphere particles was determined. The quantitativeness was confirmed by varying the concentration of the amyloid β peptide aggregates to be added. As a result, an increase was observed in the number of counts of the fluorescence positive microsphere particles, the number depending on the concentration of the added amyloid β peptide aggregates, and the quantitativeness was confirmed. FIG. 16 shows the obtained result.

Quantity Determination 2 of Amyloid β Peptide Aggregates

The above prepared anti-amyloid β antibody binding microspheres, the invention compound 1, and amyloid β peptide aggregates prepared by the same method as in test example 6 are mixed, and the mixture is caused to react for 5 to 60 minutes at 4° C. Then, fluorescence intensity analysis of the microspheres is performed by a capillary electrophoresis method. By subtracting as a background the analysis value of the negative control microspheres to which the nonspecific mouse IgG1 antibody is bound, the specific fluorescence intensity is determined. The quantitativeness can be confirmed by varying the concentration of the amyloid β peptide aggregates to be added.

INDUSTRIAL APPLICABILITY

The compound of the present invention has high affinity to an amyloid β protein, and contains many equivalent fluorine atoms that are indispensable for $^{19}$F-MRI detection. Therefore, the compound of the present invention can function as an MRI contrast medium, and can be used for a noninvasive diagnosis of a live patient of an amyloid accumulating disease, such as Alzheimer's disease, by use of an MRI device which is widely used in medical institutions.

The invention claimed is:

1. A curcumin compound or a salt thereof represented by formula (I):

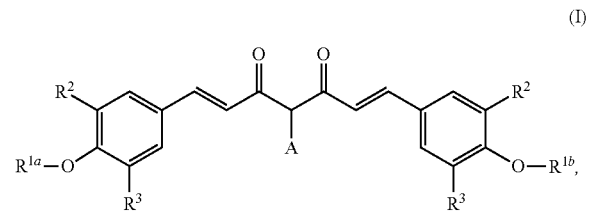

wherein $R^{1a}$ and $R^{1b}$ are each independently a hydrogen atom, alkyl, acetyl, or methoxycarbonyl; $R^2$ is each independently a fluorine atom, $CHF_2$—, $CF_3$—, $CHF_2O$, or $CF_3O$; $R^3$ is each independently a hydrogen atom or a fluorine atom; A is cyano, carboxyl, alkoxycarbonyl, or $R^4$—$(CH_2)_m$—; $R^4$ is hydroxy, carboxy, cyano, acetyloxy, alkoxycarbonyl, alkoxy, hydroxyalkoxy, or $CONR^5R^6$; $R^5$ and $R^6$ are each independently a hydrogen atom or alkyl; and m is an integer from 1 to 5.

2. A diagnostic imaging agent, for a disease in which an amyloid β protein accumulates, comprising an active component, wherein the active component is the curcumin compound or the salt thereof according to claim 1.

3. The diagnostic imaging agent according to claim 2, wherein the disease in which the amyloid β protein accumulates is Alzheimer's disease.

4. The diagnostic imaging agent according to claim 2, wherein diagnostic imaging is MRI.

5. A staining agent, for an amyloid β protein in tissue or a senile plaque in the brain, comprising an active component, wherein the active component is the curcumin compound or the salt thereof according to claim 1.

6. A method of diagnosing a disease caused in full or in part by a β-sheet structure of a protein, the method comprising:
    administering a diagnostic imaging agent comprising the curcumin compound or a salt thereof according to claim 1 to a subject, and
    detecting the compound in the subject's brain.

7. A method for staining an amyloid β protein in tissue or a senile plaque, comprising:
    staining a tissue or a senile plaque using the curcumin compound or a salt thereof according to claim 1.

* * * * *